(12) United States Patent
Carbonelli et al.

(10) Patent No.: US 11,635,416 B2
(45) Date of Patent: Apr. 25, 2023

(54) GAS SENSING DEVICE AND METHOD FOR OPERATING A GAS SENSING DEVICE

(71) Applicant: Infineon Technologies AG, Neubiberg (DE)

(72) Inventors: Cecilia Carbonelli, Munich (DE); Alexander Jesipow, Munich (DE); Alexandra Marina Roth, Neumarkt (DE); Alexander Zoepfl, Regensburg (DE)

(73) Assignee: Infineon Technologies AG, Neubiberg (DE)

( * ) Notice: Subject to any disclaimer, the term of this patent is extended or adjusted under 35 U.S.C. 154(b) by 583 days.

(21) Appl. No.: 16/838,433

(22) Filed: Apr. 2, 2020

(65) Prior Publication Data

US 2020/0355662 A1 Nov. 12, 2020

(30) Foreign Application Priority Data

May 9, 2019 (EP) ..................... 19173409

(51) Int. Cl.
*G01N 33/00* (2006.01)
*G01N 27/12* (2006.01)

(52) U.S. Cl.
CPC ....... *G01N 33/0034* (2013.01); *G01N 27/124* (2013.01); *G01N 33/0016* (2013.01)

(58) Field of Classification Search
CPC .. G06K 9/6282; G06K 9/6256; G06N 3/0445; G06N 3/08; G01N 33/0034; G01N 33/0016; G01N 33/0004; G01N 27/124
See application file for complete search history.

(56) References Cited

U.S. PATENT DOCUMENTS

2009/0126454 A1 5/2009 Pratt et al.

FOREIGN PATENT DOCUMENTS

DE 19747510 A1 5/1999

OTHER PUBLICATIONS

Boiger, Romana et al., "Exploring Temperature-Modulated Operation Mode of Metal Oxide Gas Sensors for Robust Signal Processing", MDPI, Proceedings of Eurosensors 2018, Graz, Feb. 13, 2019, pp. 5.
Carsten, Jaeschke, et al., "A Novel Modular eNose System Based on Commercial MOX Sensors to Detect Low Concentrations of VOCs for Breath Gas Analysis", MDPI, Proceedings of Eurosensors 2018, Graz, Nov. 30, 2018, pp. 4.

(Continued)

*Primary Examiner* — Christopher Adam Hixson
(74) *Attorney, Agent, or Firm* — Slater Matsil, LLP

(57) ABSTRACT

A gas sensing device includes chemo-resistive gas sensors; heating elements for heating each of the gas sensors; an information extraction block for receiving signal samples and for generating representations for the received signal samples; and a decision making block configured for receiving the representations, wherein the decision making block comprises a weighting block and a trained model based algorithm stage, wherein the weighting block receives feature samples of the representations and applies time-variant weighting functions to the feature samples of the respective representation in order to calculate a weighted representation including weighted feature samples.

21 Claims, 14 Drawing Sheets

(56) References Cited

OTHER PUBLICATIONS

Corcoran, P et al., "Optimal Configuration of a Thermally Cycled Gas Sensor Array with Neural Network Pattern Recognition", Sensors and Actuators B: Chemical, vol. 48, Issue 1-3, May 30, 1998, pp. 448-455.

Lipatov, Alexey et al., "Highly selective gas sensor arrays based on thermally reduced graphene oxide", RSC Publishing, Nanoscale, vol. 5, May 2013, pp. 5426-5434.

Vergara, A., et al., "Optimized Feature Extraction for Temperature-Modulated Gas Sensors", Hindawi Publishing Corporation, Journal of Sensors, vol. 2009, Article ID 716316, Apr. 2009, pp. 11.

Xin, Yin et al., "Temperature Modulated Gas Sensing E-Nose System for Low-Cost and Fast Detection", ResearchGate, IEEE Sensors Journal, Nov. 2015, 10 pages.

Zhang, Dongzhi, "Sensor Array Based on Metal Oxide Modified Graphene for the Detection of Multi-Component Mixed Gas", IEEE 29th International Conference on Micro Electro Mechanical Systems (MEMS), Jan. 24-28, 2016, pp. 920-923.

GAS SENSING DEVICE AND METHOD FOR OPERATING A GAS SENSING DEVICE

This application claims the benefit of European Patent Application No. 19173409, filed on May 9, 2019, which application is hereby incorporated herein by reference.

TECHNICAL FIELD

Embodiments relate to a gas sensing device for sensing one or more gases in a mixture of gases. Further embodiments relate to a method for operating such gas sensing device. More particular, the disclosure deals with the estimation of gas concentrations through the use of chemo-resistive gas sensors.

BACKGROUND

Chemical sensor algorithms are either limited to a simple model for the proof of sensor functionality, or based on a geographically distributed sensor systems.

Other existing publications describe complicated pattern analysis models based on a large amount of data obtained from geographically distributed sensor systems.

SUMMARY

A gas sensing device for sensing one or more gases in a mixture of gases is provided. The gas sensing device comprises one or more chemo-resistive gas sensors, wherein each of the gas sensors is configured for generating signal samples corresponding to a concentration of one of the one or more gases in the mixture of gases, wherein the one or more gas sensors are alternately operated in recovery phases and in sense phases, wherein at least some of the signal samples of each of the gas sensors are generated during the sense phases; one or more heating elements for heating the gas sensors according to one or more first temperature profiles during the recovery phases and according to one or more second temperature profiles during the sense phases, wherein for each of the gas sensors a maximum temperature of the respective first temperature profile is higher than a maximum temperature of the respective second temperature profile; an information extraction block configured for receiving the signal samples and for generating representations for the received signal samples for each of the gas sensors based on a plurality of features of the received signal samples of the respective gas sensor, wherein each of the features refers to a variation of dynamic characteristics of the received signal samples of the respective gas sensor over time, wherein each of the representations comprises a plurality of feature samples, wherein each of the feature samples is based on one or more of the features of the respective gas sensor; and a decision making block configured for receiving the representations, wherein the decision making block comprises a weighting block and a trained model based algorithm stage, wherein the weighting block is configured for receiving the feature samples of one of the representations and for applying one or more time-variant weighting functions to each of the feature samples of the respective representation in order to calculate for each of the representations a weighted representation comprising weighted feature samples, wherein the algorithm stage comprises an input layer and an output layer, wherein the decision making block comprises one or more trained models for the algorithm stage, wherein the weighted representations for each of the gas sensors are input to the input layer of the algorithm stage, wherein the decision making block creates for each of the gas sensors sensing results based on output values of the output layer of the algorithm stage, wherein the output values for each of the gas sensors are created by using at least one of the one or more trained models at the algorithm stage so that the output values for each of the gas sensors depend on the weighted representations of each of the gas sensors.

The one or more chemo-resistive gas sensors may be reduced graphene gas sensors, where the base material is functionalized with specific chemicals, e.g. with platinum (Pt), or manganese dioxide ($MnO_2$), so that each of the gas sensors is sensitive for a specific gas, e.g. for nitrogen dioxide ($NO_2$), ozone ($O_3$) or carbon monoxide (CO). In doing so, the interaction between graphene sheets and absorbed gas analytes influences the electronic structure of the material depending on the mixture of gases, resulting in altered charge carrier concentration and changed electrical conductance.

In case of multi-gas sensing a multi-gas sensor array comprising a plurality of chemo-resistive gas sensors having dissimilar selectivity may be used. Due to the different sensitivity towards various gas molecules, resistances of the gas sensors change in disparate patterns, making it possible to analyze complicated gas mixtures with one single sensor array.

A signal sample is a sequence consisting of time-discrete signal values, wherein the signal values are output by one of the gas sensors.

Each of the gas sensors may be heated by one or more heating elements. Each of the one or more heating elements is controlled according to a first temperature profile during the recovery phases and according to a second temperature profile during the sense phases, wherein a maximum temperature of the first temperature profile is higher than a maximum temperature of the second temperature profile.

For example, the temperature of the one or more heating elements may be pulsed between a first temperature during the recovery phases of the gas sensors and a second temperature during the sense phases of the gas sensors, wherein the first temperature is higher than the second temperature. The first temperature may be, for example, set to 300° C., whereas the second temperature may be, for example, set to 200° C.

The temperature modulation could be the same for all sensors.

In order to improve repeatability and stability of the sensing results, only the portion of the responses of the gas sensors at the lower temperatures, i.e. in a sensing phase after switching from the first temperature profile to the second temperature profile, may be considered in order to create signal samples. However, it is also possible to create signal samples at the higher temperatures, i.e. in a recovery phase after switching from the second temperature profile to the first temperature profile.

The information extraction block is configured for transforming the signal samples into representations, wherein the representations are based on dynamic characteristics of the signal samples. To this end, the pulsed nature of the responses of the gas sensors is leveraged and characteristics are extracted which rely on the dynamic evolution of the gas sensors.

The decision making block receives the representations during operational phases, wherein the decision making block comprises a weighting block and a trained model based algorithm stage.

The weighting block is configured for receiving the feature samples of one of the representations and for applying one or more time-variant weighting functions to each of the feature samples of the respective representation in order to calculate for each of the representations a weighted representation comprising weighted feature samples.

The weighting function allows to emphasize such portions of the feature samples, which contain a high degree of useful information, and to attenuate such portions of the feature samples, which contain a low degree of useful information. In particular, the weighting function allows suppressing portions of the feature samples which contain no information or redundant information. Relying on those portions of the feature samples, which contain high degree of useful information leads to a higher accuracy of the gas measurements.

Moreover, the weighting function may also discard such portions of the feature samples completely, which contain a low degree of useful information by, for example, setting the weighting function temporarily to zero. In doing so, the total amount of data may be reduced without reducing the accuracy of the measurements.

A suitable weighting function may be found by experiments or by using of artificial intelligence. The weighting function may be determined and stored at the decision-making block before an operational phase of the device. In other embodiments, the weighting function may be calculated by the decision-making block during the operational phase.

The trained model based algorithm stage is a processing stage which is capable of machine learning. The machine learning is done in a preoperational training phase in which trained models are developed by comparing actual output values of the trained model based algorithm stage with desired output values of the trained model based algorithm stage for defined inputs of the trained model based algorithm stage. The trained models have a predefined structure, wherein a parametrization of the predefined structure is done during the training phase. The trained models comprise the learned content after the training phase is finished. In an operational phase for producing sensing results one or more of the trained models from the training phase are used to process the representations from the information extraction block.

In the training phase the plurality of trained models can be established and afterwards stored at the decision-making block. The trained models may differ in the structures and/or the parameters. During operation of phase the most appropriate trained model may be selected depending on the specific use-case.

The algorithm stage comprises an input layer and an output layer, wherein the decision making block comprises one or more trained models for the algorithm stage, wherein the weighted representations for each of the gas sensors are input to the input layer of the algorithm stage, wherein the decision making block creates for each of the gas sensors sensing results based on output values of the output layer of the algorithm stage, wherein the output values for each of the gas sensors are created by using at least one of the one or more trained models at the algorithm stage so that the output values for each of the gas sensors depend on the weighted representations of each of the gas sensors.

The decision making block provides a decision on the classification of gas concentrations detected by the gas sensors or a continuous measurement of gas concentrations detected by the gas sensors. In the first case a trained model, which is trained as a classification algorithm, is used and the sensing results are alphanumeric terms such as "high" or "low". In the latter case a trained model, which is trained as a regression algorithm, is used and the sensing results are physical quantities such as "4% by volume".

The gas sensing device according to the disclosure addresses the intrinsic instability of chemo-resistive gas sensors. It uses robust algorithms and detection mechanisms which can cope with calibration inaccuracies, drifts and other similar effects reliably and over a wide operating range.

The proposed gas sensing device provides an end to end solution for multi-gas adsorption sensors which is versatile, widely-applicable to multiple applications and uses cases (outdoor, indoor, health check, etc.) and can be embedded in a smart portable device. Specifically, an algorithm is used that works on continuous sensor readings, makes use of the transient information in the sensor responses and exhibits low complexity and limited memory requirements.

The gas sensing device can reflect real world scenarios, where, for example, gas mixtures are present which are causing cross-sensitivities in the sensor responses. Moreover, the gas sensing device only takes a short time for reaching a stable response level.

The material costs of the gas sensing device are low and it uses concrete mechanisms which are robust and economic enough to be embedded into mass-produced consumer electronic products (like a mobile phone), while delivering good continuous prediction performance in complicated real world scenarios, and as such have to deal with challenges related to the availability of a limited and noisy sets of data, imperfect initial calibration, gas mixtures with varying concentrations of analytes, modelling errors, etc.

In particular, the gas sensing device may be used for air quality monitoring.

According to embodiments of the disclosure the information extraction block comprises a plurality of feature extraction stages, wherein each of the feature extraction stages is configured for calculating for one of the signal samples an output sample based on one of the features of the respective signal sample for each of the gas sensors, wherein the plurality of feature samples of one of the representations is based on the output samples of the plurality of feature extraction stages.

In order to extract relevant information out of the signal samples and transform them into feature samples, which provide meaningful data to the decision making block, a combination of feature extraction stages may be used.

According to embodiments of the disclosure the feature extraction stages, comprise a derivative calculation stage configured for calculating a derivative of the one of the signal samples for each of the gas sensors in order to produce one of the output samples for the respective signal sample.

The gas sensors are operated in adsorption phases that increase or decrease the sensor resistance depending on the gas to which the gas sensor is exposed to. This is an important sensor characteristic as it differentiates between an adsorption and desorption phase even if a sensor has the same response value in both phases. In other words, using the derivative of a filtered signal sample as a feature (Equation 1), pattern recognition algorithms are able to differentiate between adsorption and desorption phases.

$$D_{n,i} = \frac{R_{n,i+1} - R_{n,i-1}}{t_{n,i+1} - t_{n,i-1}} \qquad (1)$$

for 1≤i≤N, n=1, 2, . . . 8, where n is the sensor number, R and D are the preprocessed sensor responses and their derivatives respectively.

It has to be noted that the absorption/desorption phase information can guide in the selection of the trained model in the decision making block.

According to embodiments of the disclosure the feature extraction stages, comprise a phase space integral calculation stage configured for calculating a phase space integral of the one of the signal samples for each of the gas sensors in order to produce one of the output samples for the respective signal sample.

A phase space is a model used within dynamic systems to capture the change in a system state over time. In this phase space the temporal evolution of any system is represented by time parametric trajectories. The signal and its first time derivative are the two canonical variables commonly used to produce the phase space. For our results we used the integral of this trajectory which condenses the magnitude of the interaction with its velocity. This can be seen as the combination of the two already mentioned features, sensor response and the corresponding derivative. Containing dynamic and steady-state information, new characteristics of the sensor signals are created that a pattern recognition algorithm may not have been identified by analyzing magnitude and velocity separately. Since the integral of this trajectory distinguishes between signals with similar dynamic behavior and the same resistance shift, it can be a contributing feature to estimate both gas concentration (quantitative analysis) and class membership (qualitative analysis).

According to embodiments of the disclosure the feature extraction stages, comprise a correlation calculation stage configured for calculating of a time correlation for each of the gas sensors between the one of the signal samples and a previous signal sample of the signal samples of the respective gas sensor in order to produce one of the output samples for the respective signal sample, and/or a spatial correlation between the one of the signal samples and one of the signal samples of another of the gas sensors in order to produce one of the output samples for the respective signal sample.

Given the dynamic behavior of the gas sensors, the availability of several transient in the sensor responses and the characteristic array structure with different functionalizations, it makes sense to introduce metrics which exploits such time and spatial properties. This can be achieved introducing a time autocorrelation function of the normalized sensor responses of the type (and its derivative)

$$R_T = \sum_{k=1}^{n} x_k y_k. \quad (2)$$

Where x and y indicate the normalized response at different moments in time (or, alternatively, their derivatives) and n is the window size being used to calculate the autocorrelation. Particularly:

$$x_k = \frac{\Delta R(k)}{R_0}; x_k = \Delta R(k+\tau)/R_0. \quad (3)$$

Similarly, the correlation among the different gas sensors should also be exploited with a spatial correlation matrix of the type:

$$R_s[r, p] = \frac{1}{n}\sum_{i=1}^{n} x_{i,r} x_{i,p}. \quad (4)$$

According to embodiments of the disclosure the feature extraction stages, comprise a dynamic moment calculation stage configured for calculating of a dynamic moment of the one of the signal samples for each of the gas sensors in order to produce one of the output samples for the respective signal sample.

The phase space integral neglects the characteristic properties of the signal evolution. For example, dynamic properties resulting from different interactions taking place by sensors being exposed to different analytes are neglected by the features like derivative or integral of phase space. To this end, the shape of the trajectory in the space described by the signal response plotted against the same signal response delayed by T samples is introduced. It should be noted that the interactions with different compounds (sensor functionalization) result in different trajectories and therefore greater consistent differentiation among samples that can help pattern recognition algorithms classify multi-gas exposures.

The differences in trajectories are recorded by the following set of morphological descriptors, also known as dynamic moments. Analogous to the second moments of area of a 2-D geometrical feature, these are used to obtain the dynamic moments.

$$DM3_{PB} = \frac{\sqrt{2}}{2n} \sum_{i=1}^{n} (x_i^2 y_i - x_i y_i^2) \quad (5)$$

$$DM3_{SB} = \frac{\sqrt{2}}{2n} \sum_{i=1}^{n} [2x_i^3 + 3(x_i^2 y_i + x_i y_i^2)] \quad (6)$$

$$DM3_X = \frac{1}{2n}\sum_{i=1}^{n} (x_i^3 + 3x_i y_i^2) \quad (7)$$

$$DM3_Y = \frac{1}{2n}\sum_{i=1}^{n} (x_i^3 + 3x_i^2 y_i) \quad (8)$$

The number gives the degree of the moment, the subscript indicates the direction along which the moment is calculated, PB and SB are principle and secondary bi-sectors, is the window size being used to calculate the dynamic moments, i.e. the number of prior samples that are used to calculate the dynamic moments at the cur-rent moment in time. x and y indicate the normalized response at different moments in time as in (3).

According to embodiments of the disclosure the information extraction block is configured in such way that the feature samples of one of the representations comprise all of the output samples for the corresponding signal sample.

This is a straightforward approach which only requires low computational resources as the feature samples may be transferred to the decision-making block without further processing.

According to embodiments of the disclosure the information extraction block comprises a dimensionality reduction stage, wherein each of a plurality of the output samples of one of the signal samples is fed to the dimensionality reduction stage, wherein the dimensionality reduction stage is configured to output one or more reduced output samples based on the plurality of the output samples fed to the dimensionality reduction stage, wherein a number of the reduced output samples is smaller than a number of the output samples fed to the dimensionality reduction stage, wherein a redundancy of the reduced output samples is lower than a redundancy of the output samples fed to the dimensionality reduction stage, wherein the information extraction block is configured in such way that the feature samples of one of the representations comprise all of the reduced output samples for the corresponding signal sample.

The feature space (the dimensionality of the feature samples) may be reduced, for example to 2 or 3 dimensions. If the non-linear behavior in the reduced representation needs to be captured, an auto-encoder may be used for dimensionality reduction. An auto-encoder is an unsupervised learning algorithm that works similarly to a feed-forward neural network but instead of trying to classify an input, it is trying to reproduce the input as the output by minimizing the reconstruction error. This is particularly useful because the hidden layer of the auto-encoder has fewer neurons than the input layer.

The representation in the hidden layer (feature layer) of a 3-layer auto-encoder will produce similar results to principal component analysis except the scale of the reduced dimensions will be different. More hidden layers can help encode more complex functions of the input which can help find non-linear interdependencies among features.

Furthermore, to escape "curse of dimensionality", avoid redundancy and further reduce noise, the dimension of the extracted features may be reduced through an auto-encoder. Compared to more traditional dimensionality reduction methods such as principal component analysis and linear discriminant analysis, the use of an auto-encoder has the additional benefit of capturing also nonlinearities in the original signal representation which otherwise would be lost and cannot be exploited to discriminate the different gases.

According to embodiments of the disclosure weighting block is configured for applying one of the one or more time-variant weighting functions to all of the feature samples of the respective representation in order to calculate for each of the representations a weighted representation comprising weighted feature samples.

This is a straightforward approach which only requires low computational resources as only one time-variant weighting function is necessary in order to process the plurality of feature samples.

According to embodiments of the disclosure weighting block is configured for applying to at least some of the feature samples of the respective representation different time-variant weighting functions of the one or more time-variant weighting functions in order to calculate for each of the representations a weighted representation comprising weighted feature samples.

By these features the accuracy of the gas measurements may be increased.

According to embodiments of the disclosure the time-variant weighting functions comprise one or more window functions.

A window function (also known as an apodization function or tapering function) is a mathematical function that is zero-valued outside of some chosen interval, normally symmetric around the middle of the interval, usually near a maximum in the middle, and usually tapering away from the middle. Mathematically, when another function or waveform/data-sequence is multiplied by a window function, the product is also zero-valued outside the interval: all that is left is the part where they overlap, the "view through the window".

By using a window function the amount of data may be reduced. In particular, a rectangular window function may be used. The window function may be predefined and stored at the weighting block. Alternatively, the window function may be calculated depending on one or more feature samples which are fed to the weighting block.

According to embodiments of the disclosure the algorithm stage comprises a random decision forest using the one or more trained models.

A random decision forest is a learning method for classification, regression and other tasks that operates by constructing a multitude of decision trees at training time and outputting the class that is the mode of the classes (classification) or mean prediction (regression) of the individual trees.

According to embodiments of the disclosure the algorithm stage comprises a neural network using the one or more trained models.

An artificial neural network is a parameterized statistic model, in which a number of logistic regressions are combined non-linearly. Such systems "learn" to perform tasks by considering examples, generally without being programmed with any task-specific rules. A neural network is based on a collection of connected nodes called artificial neurons. Each connection can transmit a signal from one artificial neuron to another. An artificial neuron that receives a signal can process it and then signal additional artificial neurons connected to it. The structure of the nodes, or the hyper-parameters, of a neural network is predefined by a model and the parameters of the connections are found by training the neural network. Structure and the corresponding parameters form a trained model for the respective neural network.

According to embodiments of the disclosure the weighting block comprises a weighting function calculation block and a multiplication block, wherein the weighting function calculation block is configured for receiving the feature samples of one of the representations, wherein the weighting function calculation block is configured for calculating one or more of the time-variant weighting functions by calculating a function value for each of the one of the time-variant weighting functions for each time step of a plurality of time steps based on a corresponding set of feature values, wherein the corresponding set of feature values comprise a feature value corresponding to the respective time step from each of the feature samples, wherein the multiplication block is configured for applying to each of the feature samples of the respective representation one of the time-variant weighting functions by multiplying for each of the time steps each of the feature values corresponding to the respective time step with the function value for the respective time step in order to calculate for the one representation the weighted representation comprising weighted feature samples.

A feature sample is a sequence of feature values wherein each of the feature values corresponds to a time step of the feature samples to be processed. In the same way, the weighting function may be defined by a sequence of function values, wherein each of the function values corresponds to a time step of the feature sample to which the weighting function is applied to. In order to calculate each of the function values of the weighting function the weighting function calculation block may be based on artificial intelligence. The weighting function calculation block may contain an algorithm stage using a trained model.

The function values of the weighting function can be derived step-by-step from the feature values from the feature samples to be processed. For example, the function value for the first time step may be determined by inputting the first feature value of the first feature sample, the first feature value of the second feature sample and the first feature value of the third feature sample into the weighting function calculation block, wherein the output of the weighting function calculation block derived from said inputs is the first function value of the weighting function. Then, the function value for the second time step may be determined by inputting the second feature value of the first feature sample, the second feature value of the second feature sample and the second feature value of the third feature sample into the weighting function calculation block, wherein the output of the artificial intelligence stage derived from said inputs is the second function value of the weighting function.

The weighted feature samples then may be determined by multiplying step-by-step the function values of the weighting function with the feature values of the feature samples by using the multiplication block.

As a result, the weighting functions depend on the feature samples fed to the decision-making block. Thus, the accuracy of the gas measurements may be increased.

According to embodiments of the disclosure the neural network is a recurrent neural network, wherein the weighting function calculation block is configured for calculating the one or more of the time-variant weighting functions by calculating the function value for each of the time-variant weighting functions for each time step of the plurality of time steps based on a hidden state of the recurrent neural network.

In such embodiments, the hidden states of a recurrent neural network, of which each corresponds to one of the time steps, are additionally input to the weighting function calculation block. The hidden states refer to values of nodes of hidden layers of the recurrent neural network. The hidden states provide context for the calculation of the function values of the weighting function. Thus, the working principle of such weighting function calculation block may be referred to as "attention mechanism". By using such context, the accuracy of the gas measurements may be increased.

According to embodiments of the disclosure the weighting function calculation block comprises a feed forward neural network and a softmax block, wherein the feed forward neural network is configured for receiving the feature samples and for outputting intermediate function values based on the feature samples, and wherein the softmax block is configured for calculating the function values for the one or more time-variant weighting functions based on the intermediate function values by using a softmax function.

A feedforward neural network is an artificial neural network wherein connections between the nodes do not form a cycle. As such, it is different from recurrent neural networks.

A softmax function, also known as softargmax or normalized exponential function, is a function that takes as input a vector of K real numbers, and normalizes it into a probability distribution consisting of K probabilities. That is, prior to applying softmax, some vector components could be negative, or greater than one; and might not sum to 1; but after applying softmax, each component will be in the interval (0, 1), and the components will add up to 1, so that they can be interpreted as probabilities.

Combining the feed forward neural network and the softmax provides accurate results at low computational effort.

According to embodiments of the disclosure weighting function calculation block is configured for calculating one or more second time-variant weighting functions by calculating a second function value for one of the second time-variant weighting functions for each time step of the plurality of time steps based on a corresponding second set of feature values, wherein the corresponding second set of feature values comprise a feature value corresponding to a time step preceding the respective time step from each of the feature samples, wherein the multiplication block is configured for applying to each of the feature samples of the respective representation one of the second time-variant weighting functions by multiplying for each of the time steps each of the feature values corresponding to the time step preceding the respective time step with the second function value for the respective time step in order to calculate for the one representation second weighted feature samples, wherein the second weighted feature samples are added to the respective weighted representation.

In such embodiments each of the second time variant weighting functions depends on a set of feature values from a previous time step. Thus, the multiplication of the second time-variant weighting functions with the set of feature values from a previous time step results in second weighted feature samples, which are temporarily delayed. As the second weighted feature samples are added to the respective weighted representation, the useful amount of information in the weighted representations may be increased so that the accuracy of the gas measurements may be increased.

According to embodiments of the disclosure the neural network is a recurrent neural network, wherein the weighting function calculation block is configured for calculating the one or more second time-variant weighting functions by calculating the second function value for each of the second time-variant weighting functions for each time step of the plurality of time steps based on a hidden state of the recurrent neural network.

By using such features, the accuracy of the gas measurements may be further increased.

According to embodiments of the disclosure the weighting function calculation block comprises at least one second feed forward neural network, wherein each of the second feed forward neural networks is configured for receiving one of the second sets of feature values and for outputting second intermediate function values based on one of the second sets of feature values, and wherein the softmax block is configured for calculating the function values for the one of the time-variant weighting functions and the second function values for the one of the second time-variant weighting functions based on the intermediate function values and the second intermediate function values.

By using such features, the accuracy of the gas measurements may be further increased.

In mathematical terms, the function values and the second function values may be defined as $$\alpha_j = \frac{\exp(u_j)}{\sum_{k=1}^{T_x} \exp(u_k)}$$

$$u_j = FFNN(s_j, h_t)$$

where αj is the respective function value or second function value, sj is the signal for time step j, ht the (optional) hidden state from the recurrent neural network at time step t and Tx the number of time steps under consideration. The feed forward neural network and the second feed forward network can be dimensioned as desired, however, as there are Tx networks, smaller dimensions are preferable. For example:

$$uj=\tanh(sj*Wj+bj).$$

In case of also using the hidden state of a recurrent neural network, the equation can be changed to $$uj,=\tanh([sjht]*Wj,t+bj,t)$$

by concatenating the vectors sj and ht. The first dimension of Wj, changes accordingly.

With the two equations above, a single function value or second function value for a specific time step of the representation can be computed, irrespective of the number of features samples contained in that representation. Alternatively, one could also think of a mechanism where the function values or second function values are adjusted not only for an individual time step, but also for each feature sample at that time step.

As a last step, the input to the recurrent neural network is formed as a weighted sum of the signals at the various time steps under consideration:

$$x = \sum_{j=1}^{T_x} \alpha_j * s_j.$$

According to embodiments of the disclosure at least some of the gas sensors are heated according to different first temperature profiles of the one or more first temperature profiles during the recovery phases and/or according to different second temperature profiles of the one or more second temperature profiles during the sense phases.

In such embodiments the temperature modulation is different for different gas sensors. This allows to better exploit the different functionalizations of the base material and to improve gas separability. Similarly, multiple heater controls can be used (one for each gas sensor) or, alternatively, a single heater control in time division multiplexing with different applied voltages so as to obtain sensor specific temperature values. The result of these controlled temperature oscillations is a more dynamic behavior of the responses of the gas sensors which will be exploited by the gas sensing device as described below.

Further disclosed is a method for operating a gas sensing device for sensing one or more gases in a mixture of gases, the gas sensing device comprising one or more chemo-resistive gas sensors, wherein the method comprises the steps of: using each of the gas sensors for generating signal samples corresponding to a concentration of one of the one or more gases in the mixture of gases, wherein the one or more gas sensors are alternately operated in recovery phases and in sense phases, wherein at least some of the signal samples of each of the sensors are generated during the sense phases; heating the gas sensors by using one or more heating elements according to one or more first temperature profiles during the recovery phases and according to one or more second temperatures profile during the sense phases, wherein for each of the gas sensors a maximum temperature of the respective first temperature profile is higher than a maximum temperature of the respective second temperature profile; using an information extraction block for receiving the signal samples and for generating representations for the received signal samples for each of the gas sensors based on a plurality of features of the received signal samples SIG of the respective gas sensor, wherein each of the features refers to a variation of dynamic characteristics of the received signal samples of the respective gas sensor over time, wherein each of the representations comprises a plurality of feature samples, wherein each of the feature samples is based on one or more of the features of the respective gas sensor; using a decision making block, which comprises a weighting block and a trained model based algorithm stage and one or more trained models for the algorithm stage, wherein the algorithm stage has an input layer and an output layer, for creating for each of the gas sensors sensing results based on output values of the output layer of the algorithm stage; and using the weighting block for receiving the feature samples of one of the representations and for applying one or more time-variant weighting functions to each of the feature samples of the respective representation in order to calculate for each of the representations a weighted representation comprising weighted feature samples; wherein the weighted representations for each of the gas sensors are input to the input layer of the algorithm stage, and wherein the output values for the one or more gas sensors are created by using at least one of the one or more trained models at the algorithm stage so that the output values for each gas sensor of the one or more gas sensors depend on the weighted representations of each of the gas sensors.

BRIEF DESCRIPTION OF THE DRAWINGS

Embodiments of the present invention are described herein making reference to the appended drawings.

Figure 1:
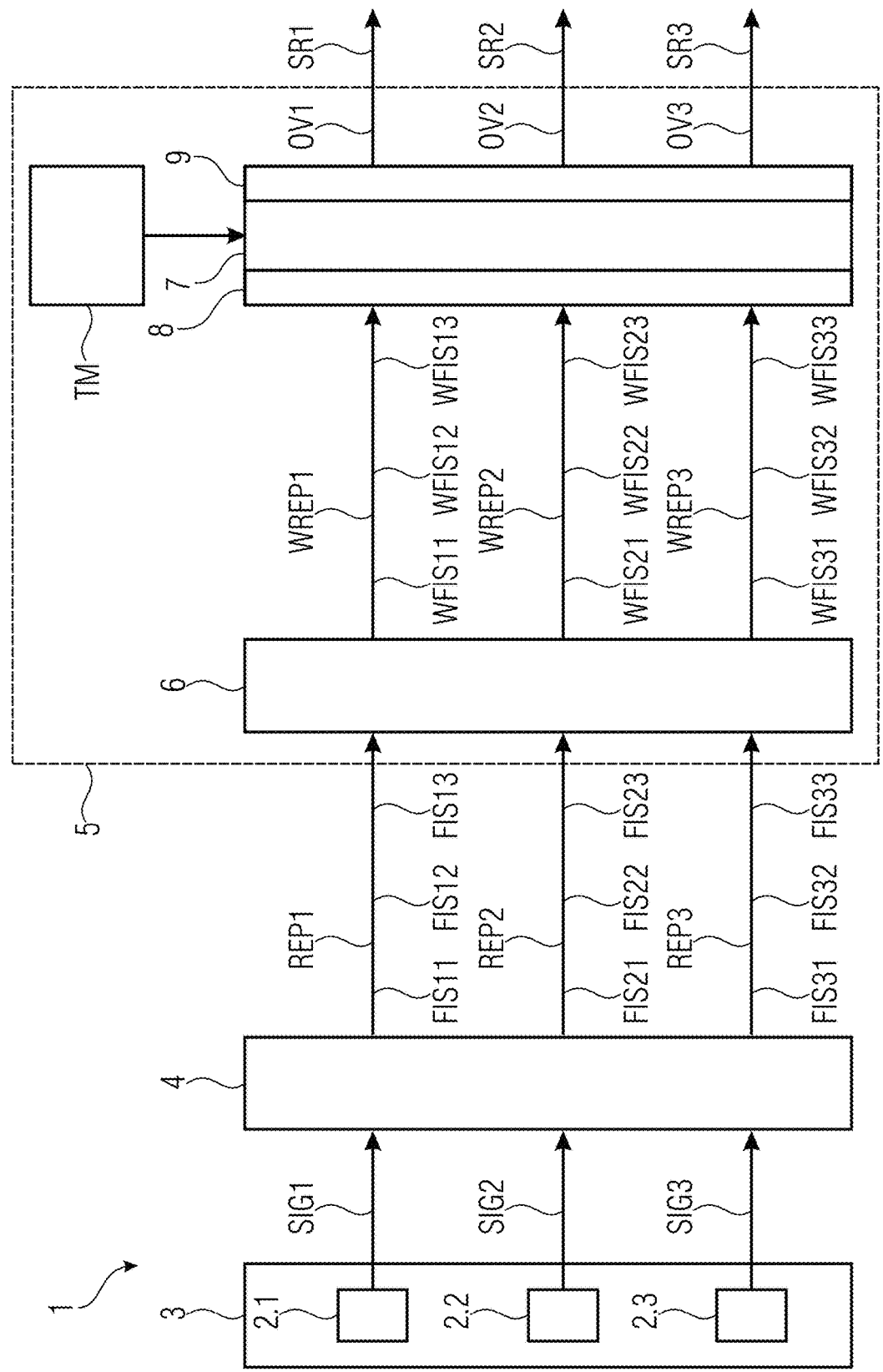
FIG. 1 shows a schematic view of a first exemplary embodiment of a gas sensing device comprising three chemo-resistive gas sensors.

Equal or equivalent elements or elements with equal or equivalent functionality are denoted in the following description by equal or equivalent reference numerals.

DETAILED DESCRIPTION OF ILLUSTRATIVE EMBODIMENTS

In the following description, a plurality of details is set forth to provide a more thorough explanation of embodiments of the present invention. However, it will be apparent to those skilled in the art that embodiments of the present invention may be practiced without these specific details. In other instances, well-known structures and devices are shown in block diagram form rather than in detail in order to avoid obscuring embodiments of the present invention. In addition, features of the different embodiments described hereinafter may be combined with each other, unless specifically noted otherwise.

FIG. 1 shows a schematic view of a first exemplary embodiment of a gas sensing device 1 for sensing one or more gases in a mixture of gases. According to embodiments of the disclosure the gas sensing device 1 comprises: one or more chemo-resistive gas sensors 2, wherein each of the gas sensors 2 is configured for generating signal samples SIG corresponding to a concentration of one of the one or more gases in the mixture of gases, wherein the one or more gas sensors 2 are alternately operated in recovery phases RP and in sense phases SP, wherein at least some of the signal samples SIG of each of the gas sensors 2 are generated during the sense phases SP; one or more heating elements 3 for heating the gas sensors 2 according to one or more first temperature profiles FTP during the recovery phases RP and according to one or more second temperature profile STP during the sense phases SP, wherein for each of the gas sensors 2 a maximum temperature of the respective first temperature profile FTP is higher than a maximum temperature of the respective second temperature profile STP; an information extraction block 4 configured for receiving the signal samples SIG and for generating representations REP for the received signal samples SIG for each of the gas sensors 2 based on a plurality of features of the received signal samples SIG of the respective gas sensor 2, wherein each of the features refers to a variation of dynamic characteristics of the received signal samples SIG of the respective gas sensor 2 over time, wherein each of the representations REP comprises a plurality of feature samples FIS, wherein each of the feature samples FIS is based on one or more of the features of the respective gas sensor 2; and a decision making block 5 configured for receiving the representations REP, wherein the decision making block 5 comprises a weighting block 6 and a trained model based algorithm stage 7, wherein the weighting block 6 is configured for receiving the feature samples FIS of one of the representations REP and for applying one or more time-variant weighting functions to each of the feature samples FIS of the respective representation REP in order to calculate for each of the representations REP a weighted representation WREP comprising weighted feature samples WFIS, wherein the algorithm stage 7 comprises an input layer 8 and an output layer 9, wherein the decision making block 5 comprises one or more trained models TM for the algorithm stage 7, wherein the weighted representations WREP for each of the gas sensors 2 are input to the input layer 8 of the algorithm stage 7, wherein the decision making block creates 5 for each of the gas sensors 2 sensing results SR based on output values OV of the output layer 9 of the algorithm stage 7, wherein the output values OV for each of the gas sensors 2 are created by using at least one of the one or more trained models TM at the algorithm stage 7 so that the output values OV for each of the gas sensors 2 depend on the weighted representations WREP of each of the gas sensors 2.

The embodiment shown in FIG. 1 comprises three chemo-resistive gas sensors 2.1, 2.2 and 2.3, wherein each of the sensors 2.1, 2.2 and 2.3 is sensitive for a specific gas. For example, the gas sensor 2.1 may be nitrogen dioxide sensor, the gas sensor 2.2 may be an ozone sensor and the gas sensor 2.3 may be a carbon monoxide sensor. In some embodiments gas sensors 2 could be used, which are all sensitive to one or more gases, like nitrogen dioxide, but which react differently. In other embodiments, the number of gas sensors could be greater or smaller than three.

The gas sensor 2.1 produces signal samples SIG1 which are transformed by the information extraction block 4 into representations REP1. Each of the representations REP1 comprises, for example, three feature samples FIS11, FIS12 and FIS13. The gas sensor 2.2 produces signal samples SIG2 which are transformed by the information extraction block 4 into representations REP2. Each of the representations REP2 comprises, for example, three feature samples FIS21, FIS22 and FIS23. The gas sensor 2.3 produces signal samples SIG3 which are transformed by the information extraction block 4 into representations REP3. Each of the representations REP3 comprises, for example, three feature samples FIS31, FIS32 and FIS33.

The weighting block 6 transforms the representations REP1, REP2 and REP3 into weighted representations WREP1, WREP2 and WREP3, wherein the weighted representation WREP1 comprises weighted feature samples WFIS11, WFIS12 and WFIS13, wherein the weighted representation WREP2 comprises weighted feature samples WFIS21, WFIS22 and WFIS23, and wherein the weighted representation WREP3 comprises weighted feature samples WFIS31, WFIS32 and WFIS33.

The weighted representations WREP1, WREP2 and WREP3 are fed to the input layer 8 of the algorithm stage 7 of the decision-making block 5. The weighted representations WREP1, WREP2 and WREP3 are simultaneously used for generating the output values OV1, OV2 and OV3 at the output layer 9 of the algorithm stage 7 by using one of the trained models TM.

The output values OV1, OV2 and OV3 may be directly used as sensing results SR1, SR2 and SR3. Alternatively the results SR1, SR2 and SR3 may be derived by post-processing of the output values OV1, OV2 and OV3, in particular a percentile filter could be used for post-processing of the output values OV1, OV2 and OV3.

In a further aspect the disclosure refers to a method for operating a gas sensing device 1 for sensing one or more gases in a mixture of gases, the gas sensing device 1 comprising one or more chemo-resistive gas sensors 2, wherein the method comprises the steps of: using each of the gas sensors 2 for generating signal samples SIG corresponding to a concentration of one of the one or more gases in the mixture of gases, wherein the one or more gas sensors 2 are alternately operated in recovery phases RP and in sense phases SP, wherein at least some of the signal samples SIG of each of the sensors 2 are generated during the sense phases SP; heating the gas sensors 2 by using one or more heating elements 3 according to one or more first temperature profiles FTP during the recovery phases RP and according to one or more second temperature profiles STP during the sense phases SP, wherein for each of the gas sensors 2 a maximum temperature of the respective first temperature profile FTP is higher than a maximum temperature of the respective second temperature profile STP; using an information extraction block 4 for receiving the signal samples SIG and for generating representations REP for the received signal samples SIG for each of the gas sensors 2 based on a plurality of features of the received signal samples SIG of the respective gas sensor 2, wherein each of the features refers to a variation of dynamic characteristics of the received signal samples SIG of the respective gas sensor 2 over time, wherein each of the representations REP comprises a plurality of feature samples, wherein each of the feature samples is based on one or more of the features of the respective gas sensor 2; using a decision making block 5, which comprises a weighting block 6 and a trained model based algorithm stage 7 and one or more trained models TM for the algorithm stage 7, wherein the algorithm stage 7 has an input layer 8 and an output layer 9, for creating for each of the gas sensors 2 sensing results SR based on output values OV of the output layer 9 of the algorithm stage 7; and using the weighting block 5 for receiving the feature samples FIS of one of the representations REP and for applying one or more time-variant weighting functions WF to each of the feature samples FIS of the respective representation REP in order to calculate for each of the representations REP a weighted representation WREP comprising weighted feature samples WFIS; wherein the weighted representations WREP for each of the gas sensors 2 are input to the input layer 8 of the algorithm stage 7, and wherein the output values OV for the one or more gas sensors 2 are created by using at least one of the one or more trained models TM at the algorithm stage 7 so that the output values OV for each gas sensor 2 of the one or more gas sensors 2 depend on the weighted representations WREP of each of the gas sensors 2.

Figure 2:
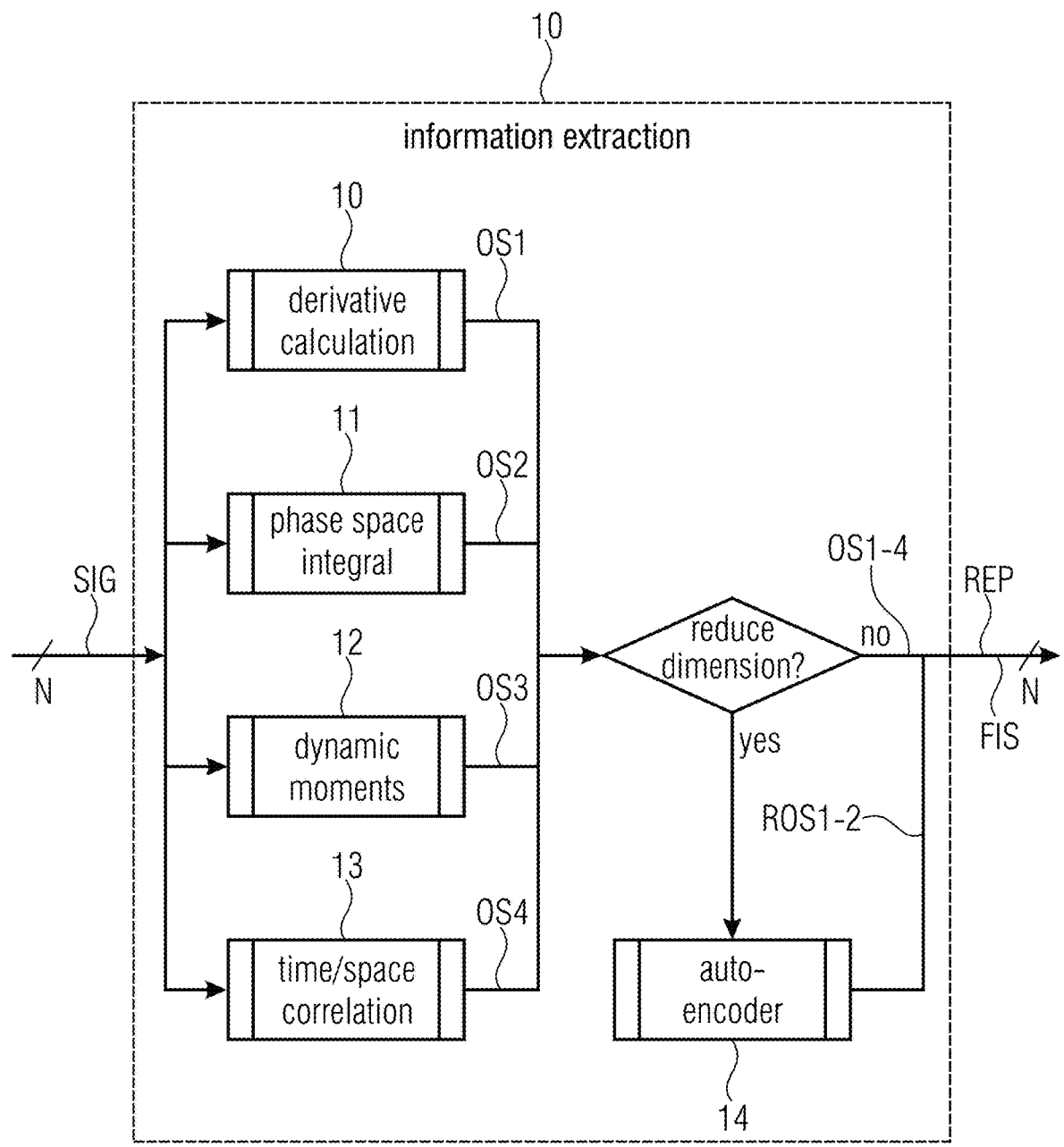
FIG. 2 shows a schematic view of an exemplary information extraction block of the gas sensing device.

FIG. 2 shows a schematic view of an exemplary information extraction block 4 of the gas sensing device 1.

According to embodiments of the disclosure the information extraction block 4 comprises a plurality of feature extraction stages 10, 11, 12, 13, wherein each of the feature extraction stages 10, 11, 12, 13 is configured for calculating for one of the signal samples SIG an output sample OS based on one of the features of the respective signal sample SIG for each of the gas sensors 2, wherein the plurality of feature samples FIS of one of the representations REP is based on the output samples OS of the plurality of feature extraction stages 10, 11, 12, 13.

According to embodiments of the disclosure the feature extraction stages 10, 11, 12, 13 comprise a derivative calculation stage 10 configured for calculating a derivative of the one of the signal samples SIG for each of the gas sensors 2 in order to produce one of the output samples OS for the respective signal sample SIG.

According to embodiments of the disclosure the feature extraction stages 10, 11, 12, 13 comprise a phase space integral calculation stage 11 configured for calculating a phase space integral of the one of the signal samples SIG for each of the gas sensors 2 in order to produce one of the output samples OS for the respective signal sample SIG.

According to embodiments of the disclosure the feature extraction stages 10, 11, 12, 13 comprise a correlation calculation stage 13 configured for calculating of a time correlation for each of the gas sensors 2 between the one of the signal samples SIG and a previous signal sample SIG of the signal samples SIG of the respective gas sensor 2 in order to produce one of the output samples OS for the respective signal sample SIG, and/or a spatial correlation between the one of the signal samples SIG and one of the signal samples SIG of another of the gas sensors 2 in order to produce one of the output samples OS for the respective signal sample SIG.

According to embodiments of the disclosure the feature extraction stages 10, 11, 12, 13 comprise a dynamic moment calculation stage 12 configured for calculating of a dynamic moment of the one of the signal samples SIG for each of the gas sensors 2 in order to produce one of the output samples OS for the respective signal sample SIG.

According to embodiments of the disclosure the information extraction block 4 is configured in such way that the feature samples FIS of one of the representations REP comprise all of the output samples OS for the corresponding signal sample SIG.

According to embodiments of the disclosure the information extraction block 4 comprises a dimensionality reduction stage 14, wherein each of a plurality of the output samples OS of one of the signal samples SIG is fed to the dimensionality reduction stage 14, wherein the dimensionality reduction stage 14 is configured to output one or more reduced output samples ROS based on the plurality of the output samples OS fed to the dimensionality reduction stage 14, wherein a number of the reduced output samples ROS is smaller than a number of the output samples OS fed to the dimensionality reduction stage 14, wherein a redundancy of the reduced output samples ROS is lower than a redundancy of the output samples fed to the dimensionality reduction stage 14, wherein the information extraction block 4 is configured in such way that the feature samples FIS of one of the representations REP comprise all of the reduced output samples ROS for the corresponding signal sample SIG.

Figure 3:
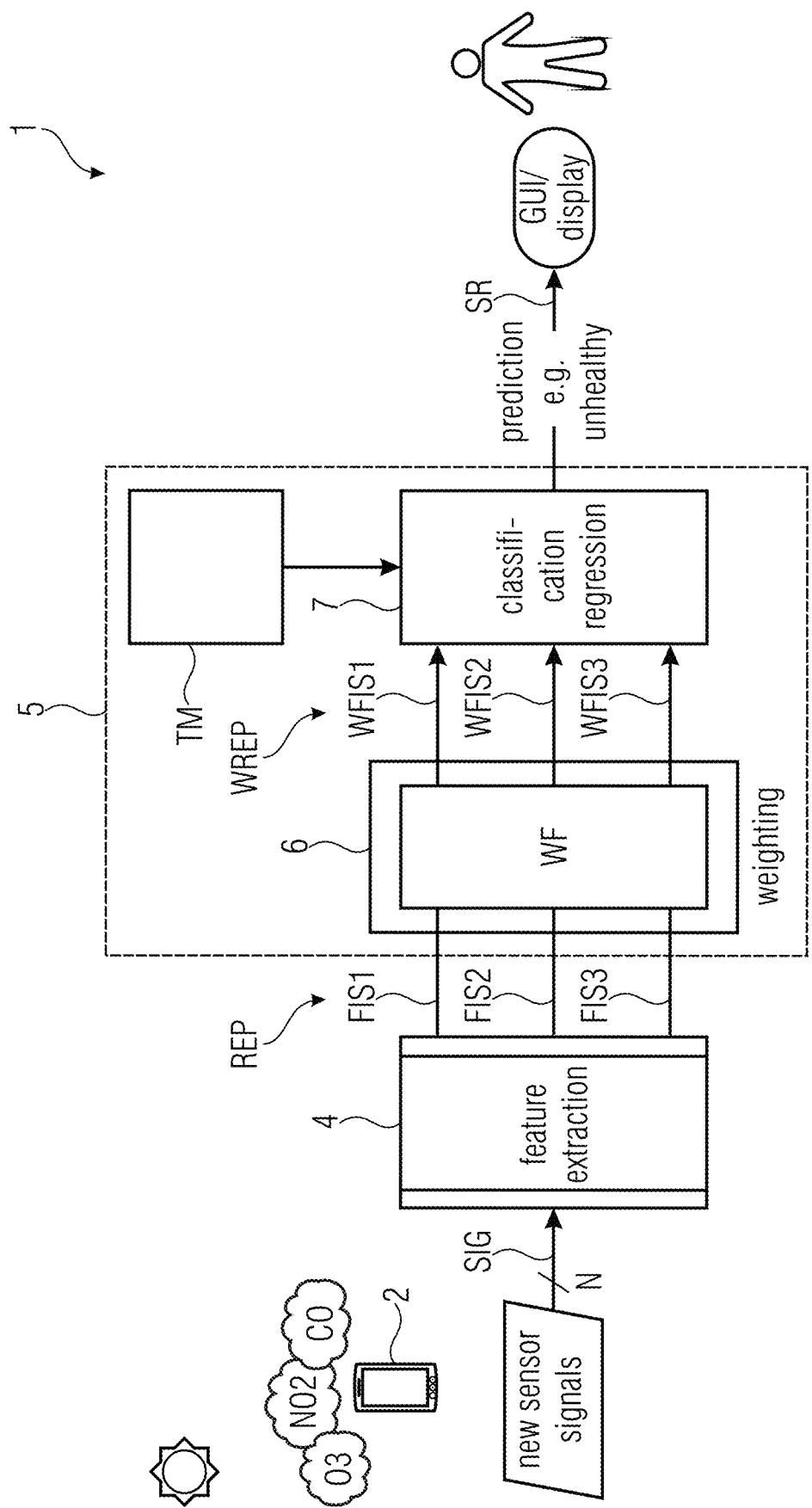
FIG. 3 shows a schematic view of a second exemplary embodiment of a gas sensing device.

FIG. 3 shows a schematic view of a second exemplary embodiment of a gas sensing device 1. According to embodiments of the disclosure the weighting block 6 is configured for applying one of the one or more time-variant weighting functions WF to all of the feature samples FIS of the respective representation REP in order to calculate for each of the representations REP a weighted representation WREP comprising weighted feature samples WFIS.

As shown in FIG. 3 the sensing results SR may be shown on a GUI or a display.

According to embodiments of the disclosure the time-variant weighting functions WF comprise one or more window functions. The window functions may be rectangular window functions. The window function may be, for example, designed for the derivative feature samples FIS in such way that the first and the last part of the sense part of the temperature pulse are used, where the signal samples SIG has a larger dynamic. For the normalized resistance feature samples one would consider the final part of the sensing phase in order to reduce the signal footprint and have the signal concentrate on a denser region.

Figure 4:
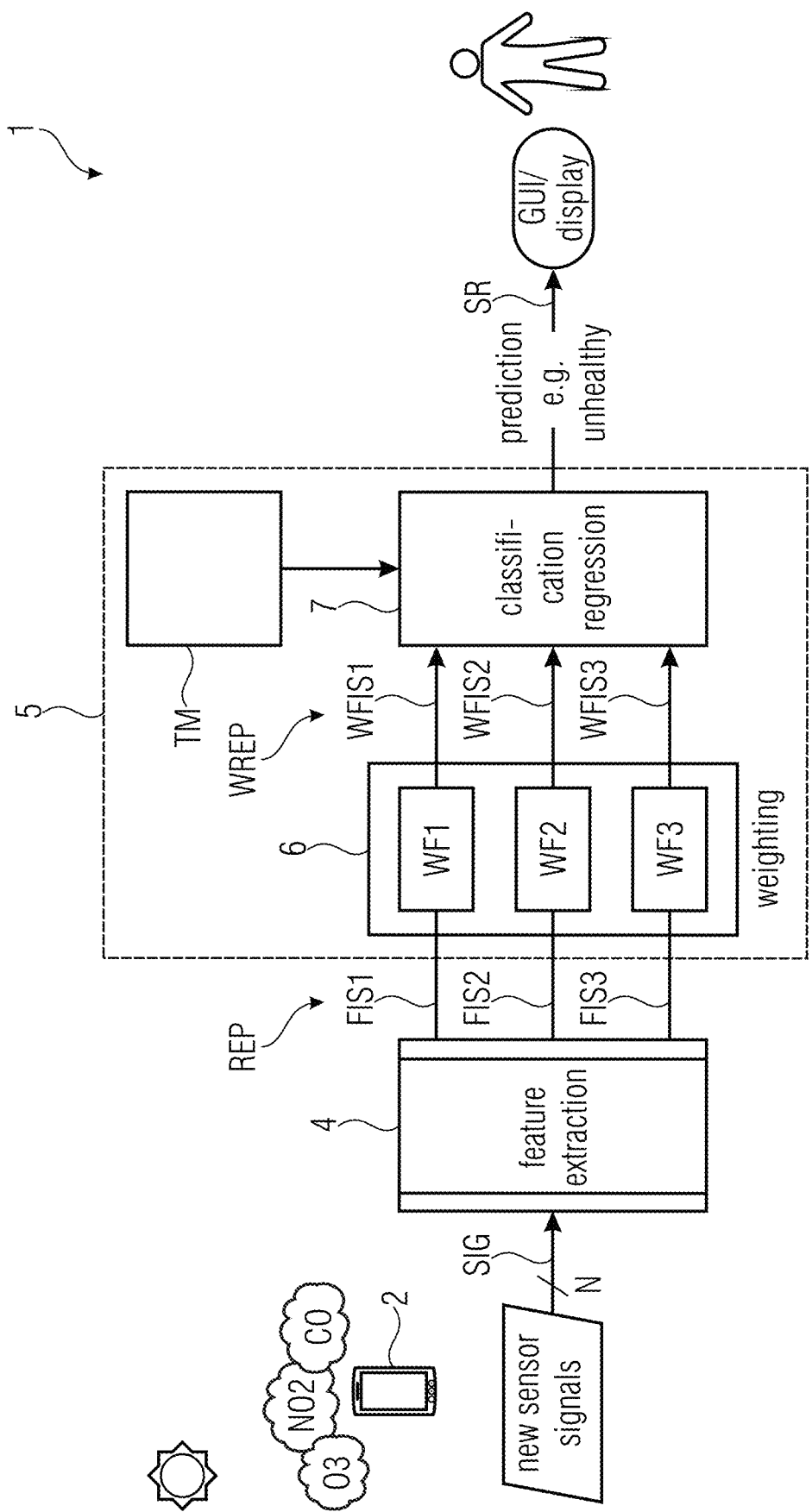
FIG. 4 shows a schematic view of a third exemplary embodiment of a gas sensing device.

FIG. 4 shows a schematic view of a third exemplary embodiment of a gas sensing device 1. According to embodiments of the disclosure the weighting block 6 is configured for applying to at least some of the feature samples FIS of the respective representation REP different time-variant weighting functions WF of the one or more time-variant weighting functions WF in order to calculate for each of the representations REP a weighted representation WREP comprising weighted feature samples WFIS.

Figure 5:
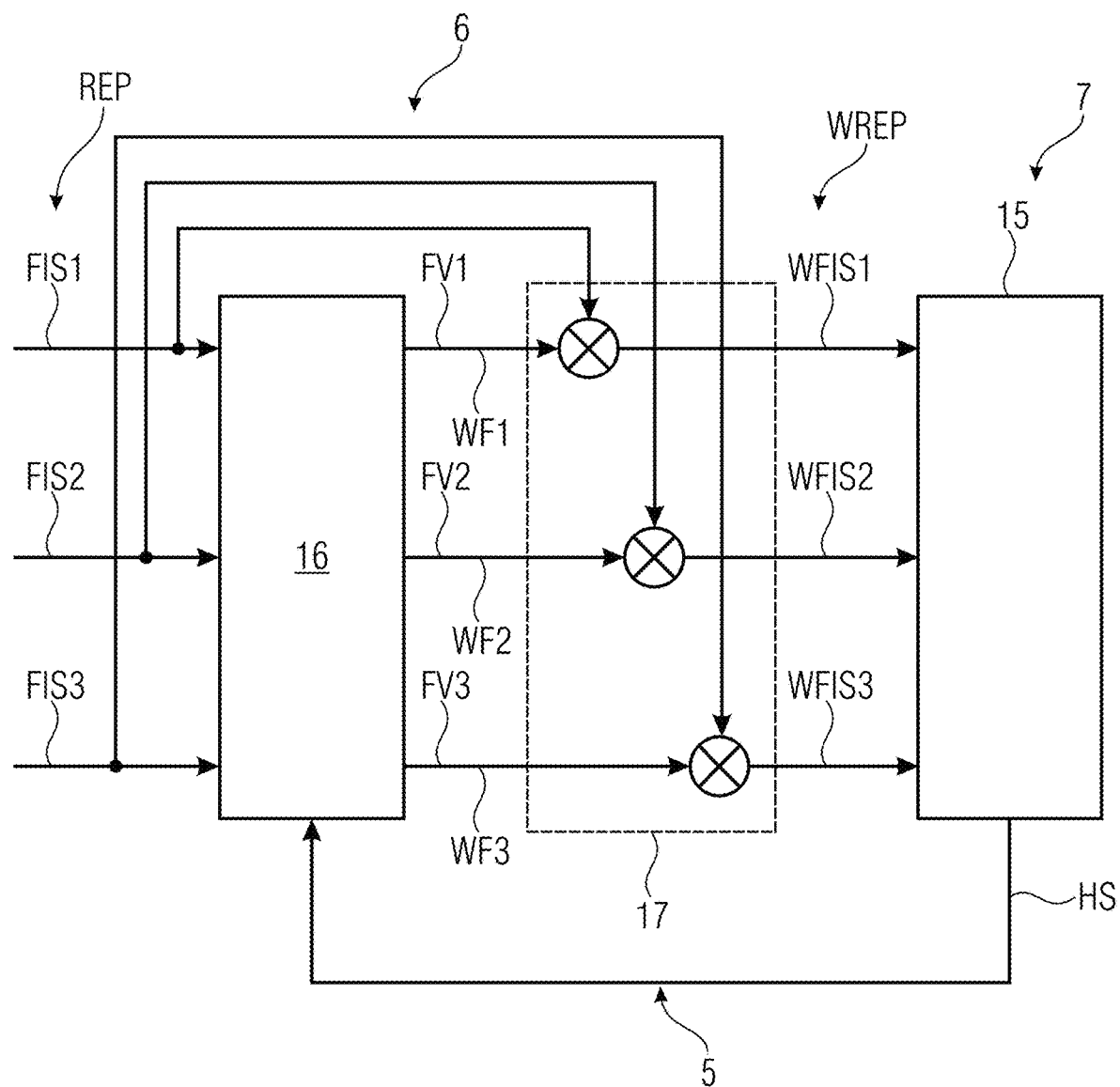
FIG. 5 shows a schematic view of an exemplary decision making block of a gas sensing device.

FIG. 5 shows a schematic view of an exemplary decision making block 6 of a gas sensing device 1. According to embodiments of the disclosure the algorithm stage 7 comprises a random decision forest using the one or more trained models TM.

According to embodiments of the disclosure the algorithm stage 7 comprises a neural network 15 using the one or more trained models TM.

According to embodiments of the disclosure the weighting block 6 comprises a weighting function calculation block 16 and a multiplication block 17, wherein the weighting function calculation block 16 is configured for receiving the feature samples FIS of the representations REP, wherein the weighting function calculation block 16 is configured for calculating one or more of the time-variant weighting functions WF by calculating a function value FV for each of the one of the time-variant weighting functions WF for each time step of a plurality of time steps based on a corresponding set of feature values, wherein the corresponding set of feature values comprise a feature value corresponding to the respective time step from each of the feature samples FIS, and wherein the multiplication block 17 is configured for applying to each of the feature samples FIS of the respective representation REP one of the time-variant weighting functions WF by multiplying for each of the time steps each of the feature values corresponding to the respective time step with the function value for the respective time step in order to calculate for the one representation REP the weighted representation WREP comprising weighted feature samples WFIS.

According to embodiments of the disclosure the neural network 15 is a recurrent neural network 15, wherein the weighting function calculation block 16 is configured for calculating the one or more of the time-variant weighting functions WF by calculating the function value FV for each of the time-variant weighting functions WF for each time step of the plurality of time steps based on a hidden state HS of the recur-rent neural network.

As an evolution of the mechanism shown FIG. 3, it's proposed to make use of recur-rent neural networks in combination with weighting function calculation block 16. The recurrent neural network 15 uses not only the last but several previous responses to make a prediction.

Figure 6:
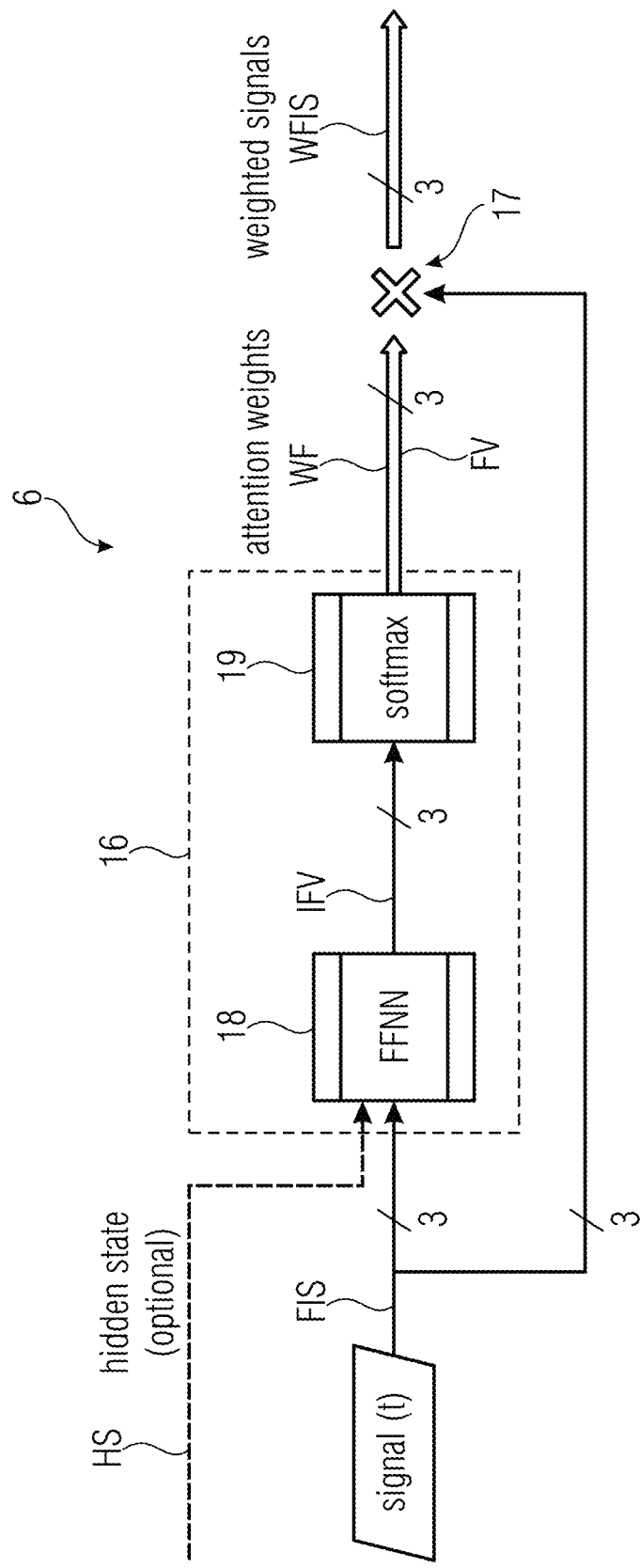
FIG. 6 shows a schematic view of an exemplary weighting block of the gas sensing device.

FIG. 6 shows a schematic view of an exemplary weighting block of the gas sensing device. According to embodiments of the disclosure the weighting function calculation block 16 comprises a feed forward neural network 18 and a softmax block 19, wherein the feed forward neural network 18 is configured for receiving the sets of feature samples FIS and for outputting intermediate function values IFV based on the feature samples FIS, and wherein the softmax block 19 is configured for calculating the function values FV for the one or more time-variant weighting functions WV based on the intermediate function values IFW by using a softmax function.

As illustrated in FIG. 6, the weighting function calculation block 16 applies different weights FV to the three feature samples FIS. The weights FV are computed with a feed forward neural network 18, which take as input the feature samples FIS as well as recurrent neural network 15 hidden state HS of the previous time step. The output of the weighting function calculation block 16 is then fed into the recurrent neural network 15, which, at the final step, outputs the predicted gas concentrations.

Figure 7:
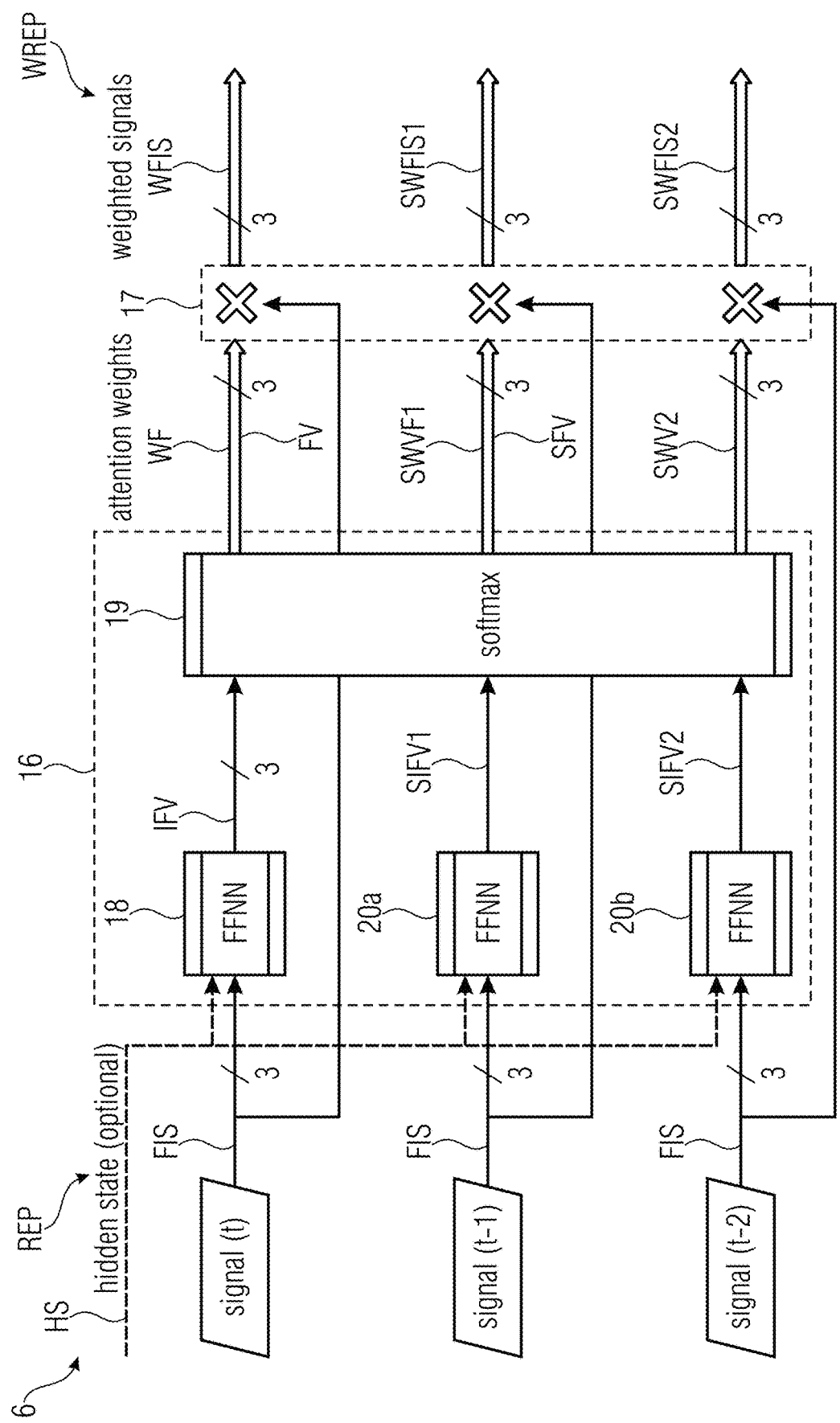
FIG. 7 shows a schematic view of a further exemplary weighting block of the gas sensing device.

FIG. 7 shows a schematic view of a further exemplary weighting block of the gas sensing device. According to embodiments of the disclosure the weighting function calculation block 16 is configured for calculating one or more second time-variant weighting functions SWF by calculating a second function value SFW for one of the second time-variant weighting functions SWF for each time step of the plurality of time steps based on a corresponding second set of feature values, wherein the corresponding second set of feature values comprise a feature value corresponding to a time step preceding the respective time step from each of the feature samples FIS, wherein the multiplication block 17 is configured for applying to each of the feature samples of the respective representation REP one of the second time-variant weighting functions SWF by multiplying for each of the time steps each of the feature values corresponding to the time step preceding the respective time step with the second function value SFW for the respective time step in order to calculate for the one representation REP second weighted feature samples SWFIS, wherein the second weighted feature samples are added to the respective weighted representation WREP.

According to embodiments of the disclosure the neural network 15 is a recurrent neural network, wherein the weighting function calculation block 16 is configured for calculating the one or more second time-variant weighting functions SWFIS by calculating the second function value SFV for each of the second time-variant weighting functions SWFIS for each time step of the plurality of time steps based on a hidden state HS of the recurrent neural network.

According to embodiments of the disclosure the weighting function calculation block 16 comprises at least one second feed forward neural network 20, wherein each of the second feed forward neural network 20 is configured for receiving one of the second sets of feature values and for outputting second intermediate function values SIFV based on one of the second sets of feature values, and wherein the softmax block 19 is configured for calculating the function values for the one of the time-variant weighting functions and the second function values for the one of the second time-variant weighting functions based on the intermediate function values IFV and the second intermediate function values SIFV.

In the example of FIG. 7 the weighting function calculation block 16 comprise the feed forward neural network 18 and the second feed forward neural networks 20a and 20b. However, the number of the second feed forward neural networks could be different from two. All of the feed forward neural networks 18, 20a and 20b may be of the same type. The feature samples FIS are fed to the feed forward neural network 18 and the second feed forward neural networks 20a and 20b. However, at the present time step the feed forward neural network 18 processes the present value of the feature sample FIS, whereas the second feed forward neural network 20a uses the value of the feature sample FIS of the previous time step, and whereas the second feed forward neural network 20b uses the value of the feature sample FIS of the time step previous to the previous time step.

In mathematical terms, the weights FV and SVF may be defined as $$\alpha_j = \frac{\exp(u_j)}{\sum_{k=1}^{Tx} \exp(u_k)}$$

$$u_j = FFNN(s_j, h_t)$$

where $\alpha_j$ is the respective weight, sj is the signal for time step j, ht the (optional) hidden state HS from the recurrent neural network 15 at time step t and Tx the number of time steps under consideration. The feed forward neural networks 18, 20a, 20b can be dimensioned as desired, however, as there are Tx networks, smaller dimensions are preferable. For example:

$$uj = \tanh(sj * Wj + bj).$$

In case of also using the hidden state of a RNN, the equation can be changed to $$uj,_t = \tanh([sj ht] * Wj,t + bj,t)$$

by concatenating the vectors sj and ht. The first dimension of Wj, changes accordingly.

With the two equations above, a single weight for a specific time step of the representation REP can be computed, irrespective of the number of features samples contained in that representation REP. Alternatively, one could also think of a mechanism where the weights FV, SFW are adjusted not only for an individual time step, but also for each feature sample FIS at that time step.

As a last step, the input to the recurrent neural network 15 is formed as a weighted sum of the signals WFIS, SWFIS1 and SWFIS2 at the various time steps under consideration:

$$x = \sum_{j=1}^{T_x} \alpha_j * s_j.$$

Figure 8:
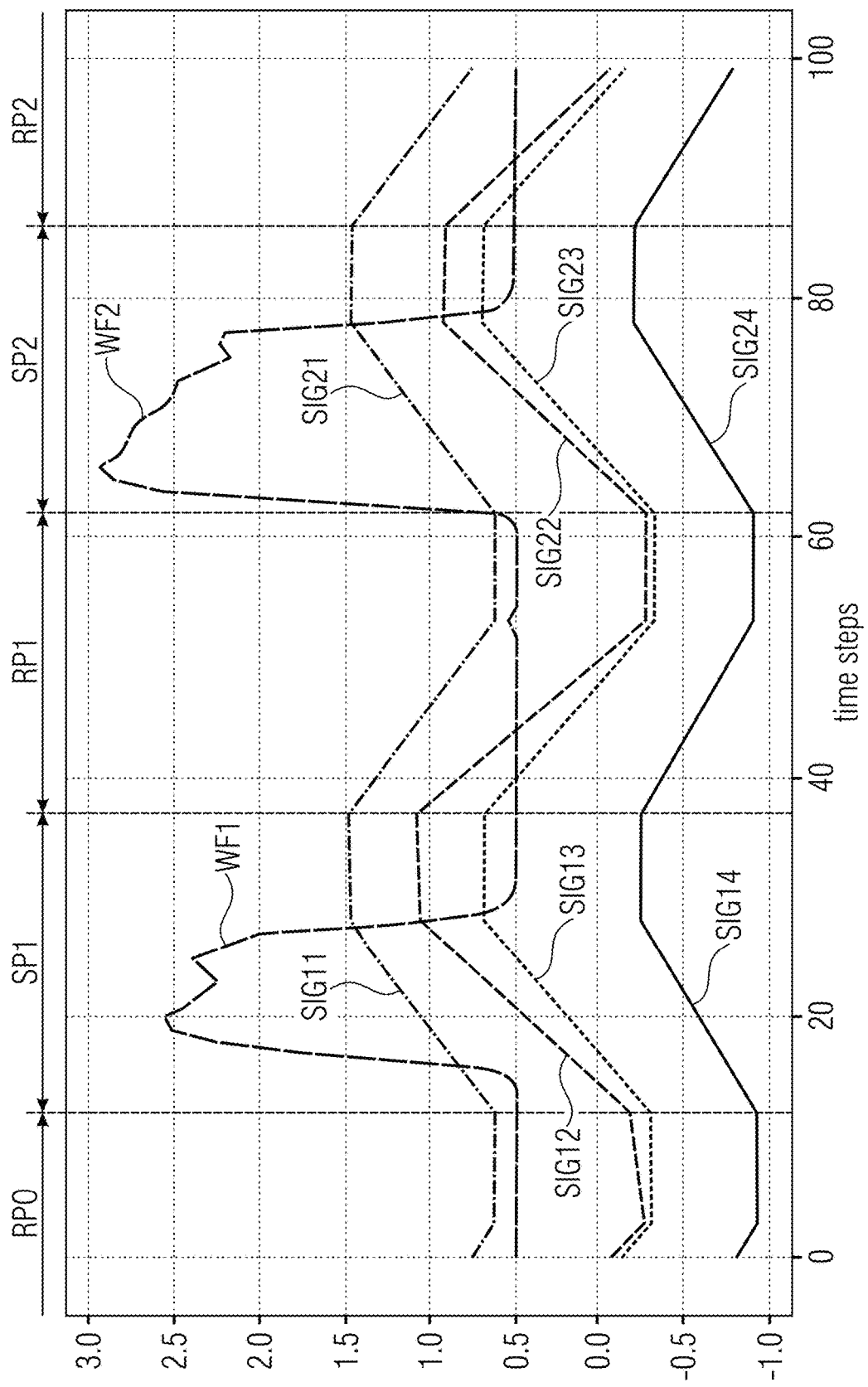
FIG. 8 illustrates exemplary signal samples and weighting functions over time.

FIG. 8 illustrates exemplary signal samples SIG and weighting functions WF over time. The timeline illustrates, in this order, a recovery phase RP0, a sensing phase SP1, a recovery phase RP1, a sensing phase SP1 and a recovery phase RP2. The signal samples SIG11, SIG12 and SIG13 are produced during the sensing phase SP1, whereas the signal samples SIG21, SIG22 and SIG23 are produced during the sensing phase SP2. The weighting function WF1 is used during sensing phase SP1 and the weighting function WF2 is used during sensing phase SP2.

The weighting function calculation block 16 allows the device 1 to emphasize each of the signal samples SIG differently, thus learning the most relevant portions of the signal samples SIG dynamically. As shown in FIG. 8, the weights generated by the attention mechanism can also be plotted which enables the designer of the system to gain an insight about what the device 1 has learned. This can be seen as an evolution of the simpler selection mechanism using window functions, as here the right signal portions are learnt directly by the weighting function calculation block 16.

Figure 9:
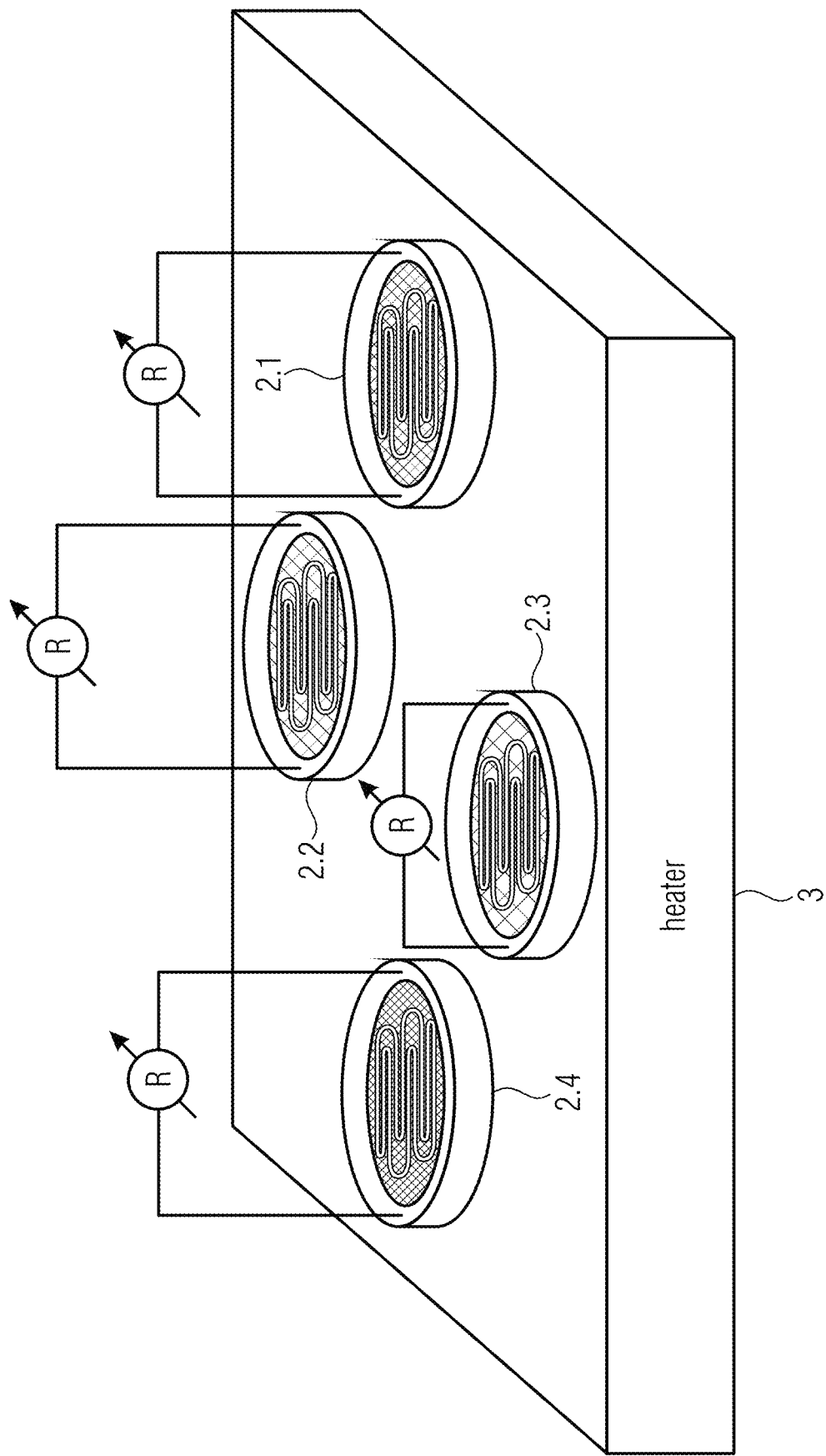
FIG. 9 shows an exemplary graphene multi-gas sensor array.

FIG. 9 shows an exemplary graphene multi-gas sensor array. Each sensor 2.1, 2.2, 2.3 and 2.4 in the array has a heating element 3 whose temperature is being pulsed between T1. (recovery phase) and T2 (sense phase). The result of these controlled temperature oscillations is a more dynamic behavior of the sensor responses as shown in FIG. 10 which is exploited by the device 1.

Several implementations of temperature pulsing mechanism are possible. For example, the temperature modulation could be the same for all sensors 2.1, 2.2, 2.3 and 2.4 or different in order to better exploit the different functionalizations of the base material and to improve gas separability. Similarly, multiple heater controls can be used (one for each sensor 2.1, 2.2, 2.3 and 2.4) or, alternatively, a single heater control in time division multiplexing with different applied voltages so as to obtain sensor specific temperature values.

Figure 10:
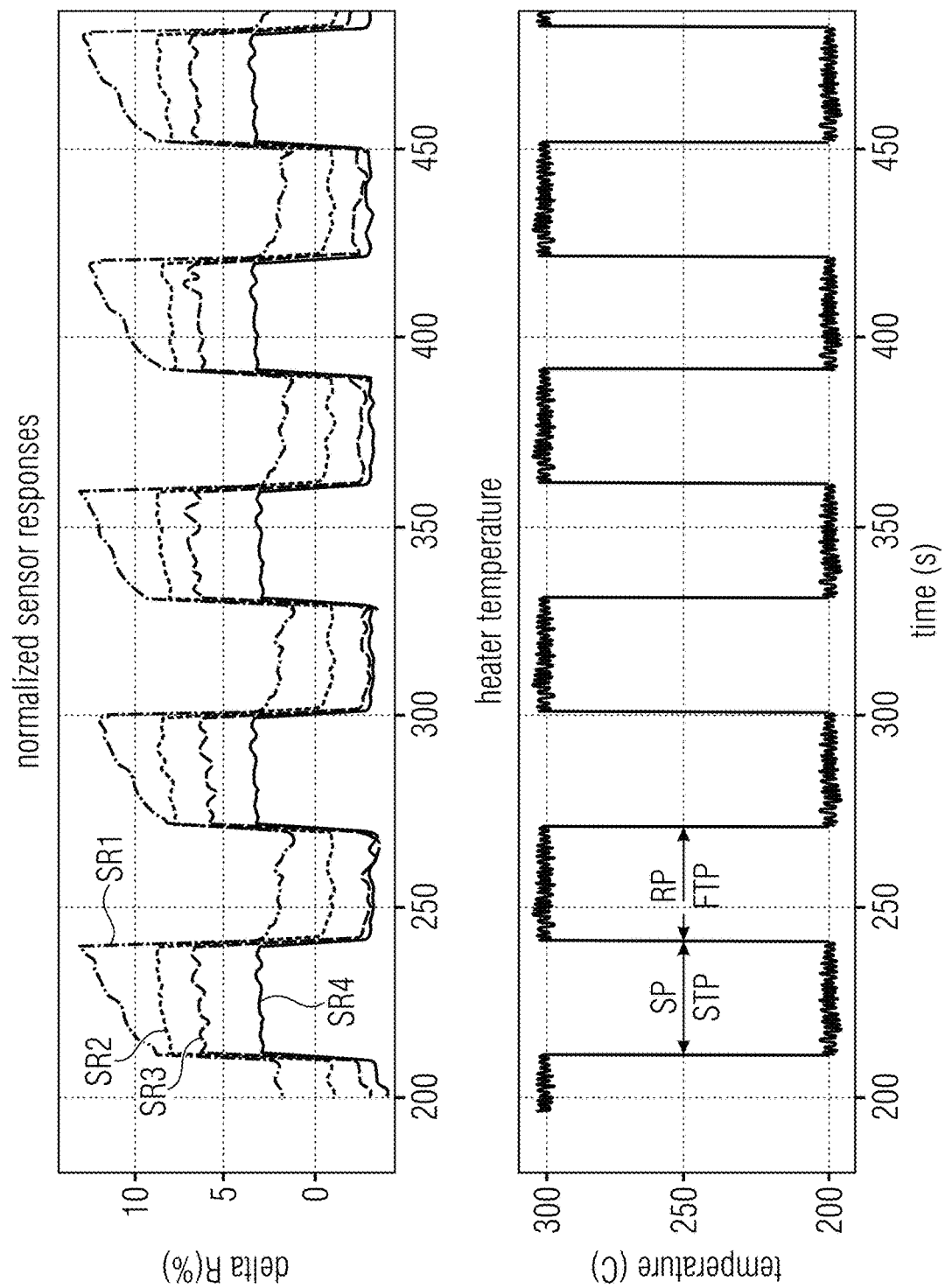
FIG. 10 illustrates exemplary normalized sensor responses and heater temperatures over time.

FIG. 10 illustrates exemplary normalized sensor responses and heater temperatures over time. In the particular example of FIG. 10 two temperatures profiles are chosen: A first temperature profile FTP for sensing the gas adsorption at a certain temperature of 200° C. during a sensing phase SP and a second temperature profile STP for recovering the sensors surface and desorb adsorbed gas molecules at 300° C. in a recovery phase RP. Therefore, not only static features like absolute or relative resistance changes can be monitored, but also dynamic features like e.g. the slope of the sense phase SP at 200° C. which reflects the gas adsorption over time. Additional temperature steps and pulse modes are also possible, as long as they contribute additional information or features to the sensing responses SR1, SR2, SR3 and SR4 like gas adsorption/reaction at a certain temperature or temperature ramp.

According to embodiments of the disclosure at least some of the gas sensors 2 are heated according to different first temperature profiles FTP of the one or more first temperature profiles FTP during the recovery phases RP and/or according to different second temperature profiles STP of the one or more second temperature profiles STP during the sense phases SP.

Figure 11:
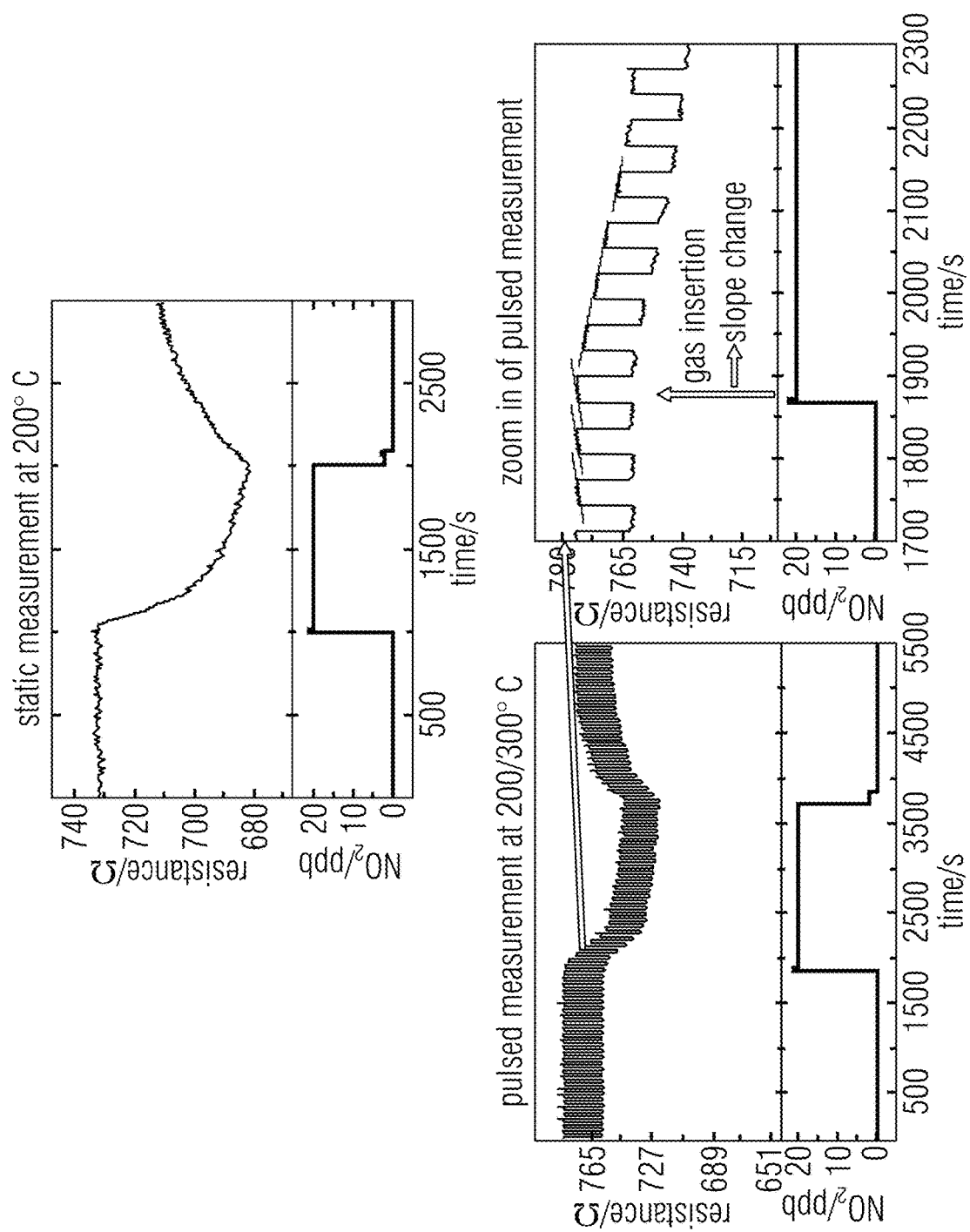
FIG. 11 illustrates exemplary sensor responses in static and pulsed measurement modes.

FIG. 11 illustrates exemplary sensor responses in static and pulsed measurement modes. Comparing sensor operation at a static temperature and pulsing between two temperatures, the major advantages get visible in FIG. 11. First of all the regeneration of the signal gets faster by implementing a recovery pulse at 300° C. But the most important feature is the immediate change of a dynamic feature like the slope after gas insertion as shown in FIG. 11, right compared to the slow change of the absolute resistance value of a sensor element as shown in Figure ii, left. This also leads to a faster signal generation or response time of the system.

Figure 12:
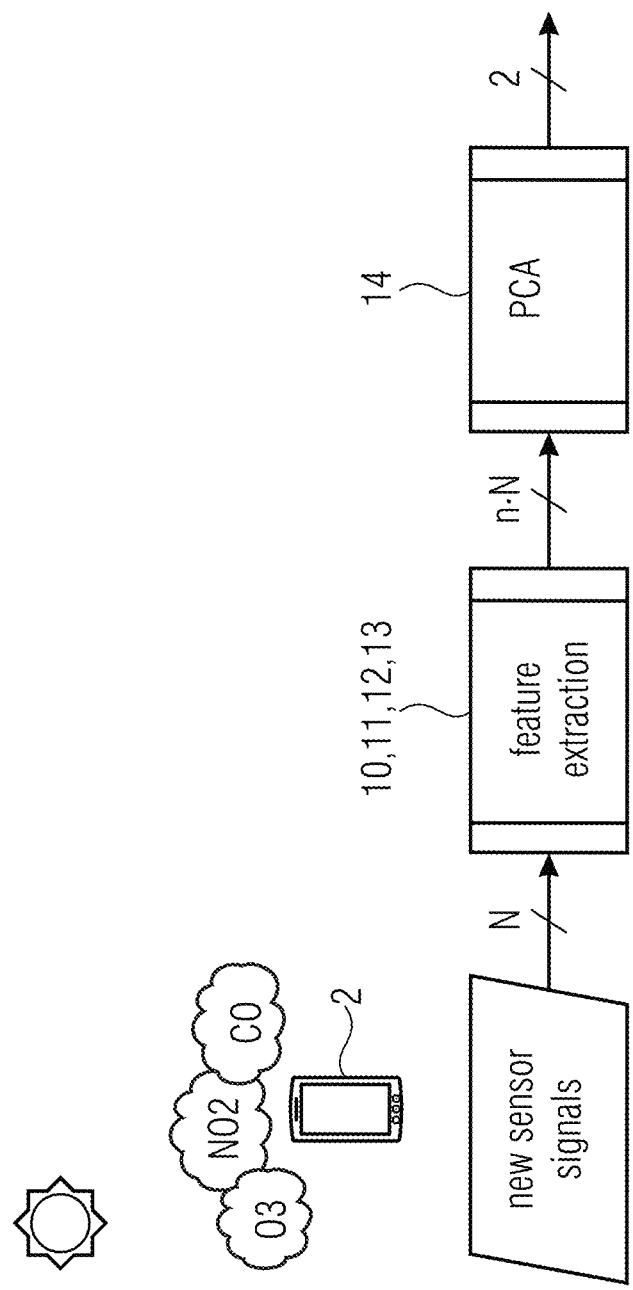
FIG. 12 shows an exemplary device for generating of scatter plots for analyses.

FIG. 12 shows an exemplary device for generating of scatter plots for analyses. On the algorithm side the above temperature modulation can also be judiciously exploited. As mentioned before, the sensing device 1 comprises an information extraction block 4, where the sensor responses may be transformed and 'coded' into feature samples FIS with the appropriate reduced dimensionality and at the same time the most informative content and a decision making block 5, where a decision on the air quality level or a continuous estimation of the gas concentration is provided resorting to a classification or regression algorithm, respectively.

To better understand the role of the information extraction block 4 it is useful to resort to a scatter plot representation of the singles features for the N=4 sensors 2 of the array. To simplify visualization a principal component analysis on the feature samples of the four sensors 2 may be performed so as to obtain a two-dimensional representation of the feature space.

Figure 13:
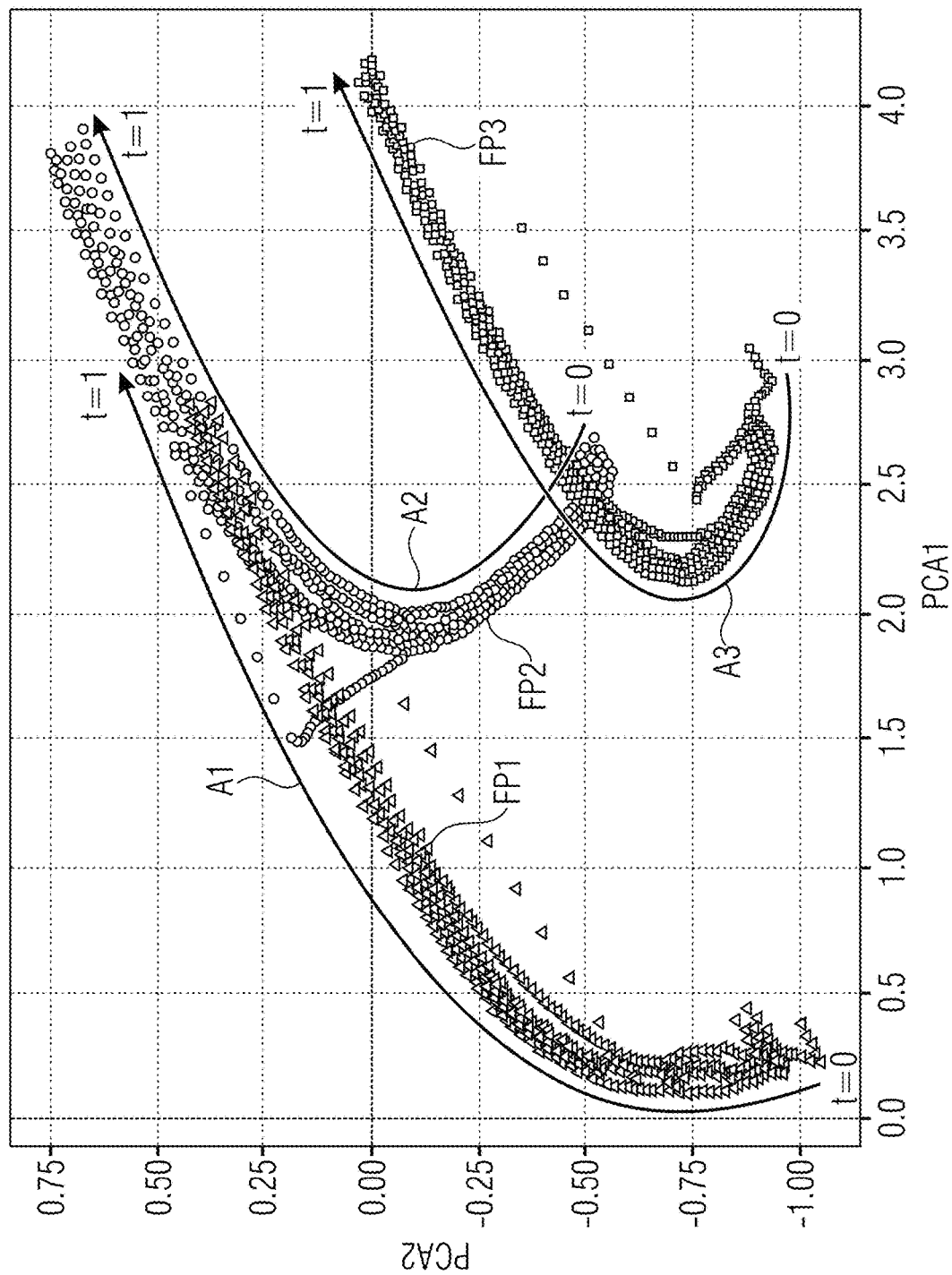
FIG. 13 illustrates a scatter plot for three different gases.

FIG. 13 illustrates a scatter plot for three different gases. The scatter plot shows the footprints FP1, FP2 and FP3 of three gases in the two-dimensional representation of the feature space. The arrows A1, A2 and A3 indicate the dependency of the elements of the footprints FP1, FP2 and FP3 on time during a sensing phase SP which starts at t=0 and ends at t=1. It is seen that, depending on the specific features, different portions of the sense phase SP should be selected to ensure better separability of gases and concentrations.

Figure 14:
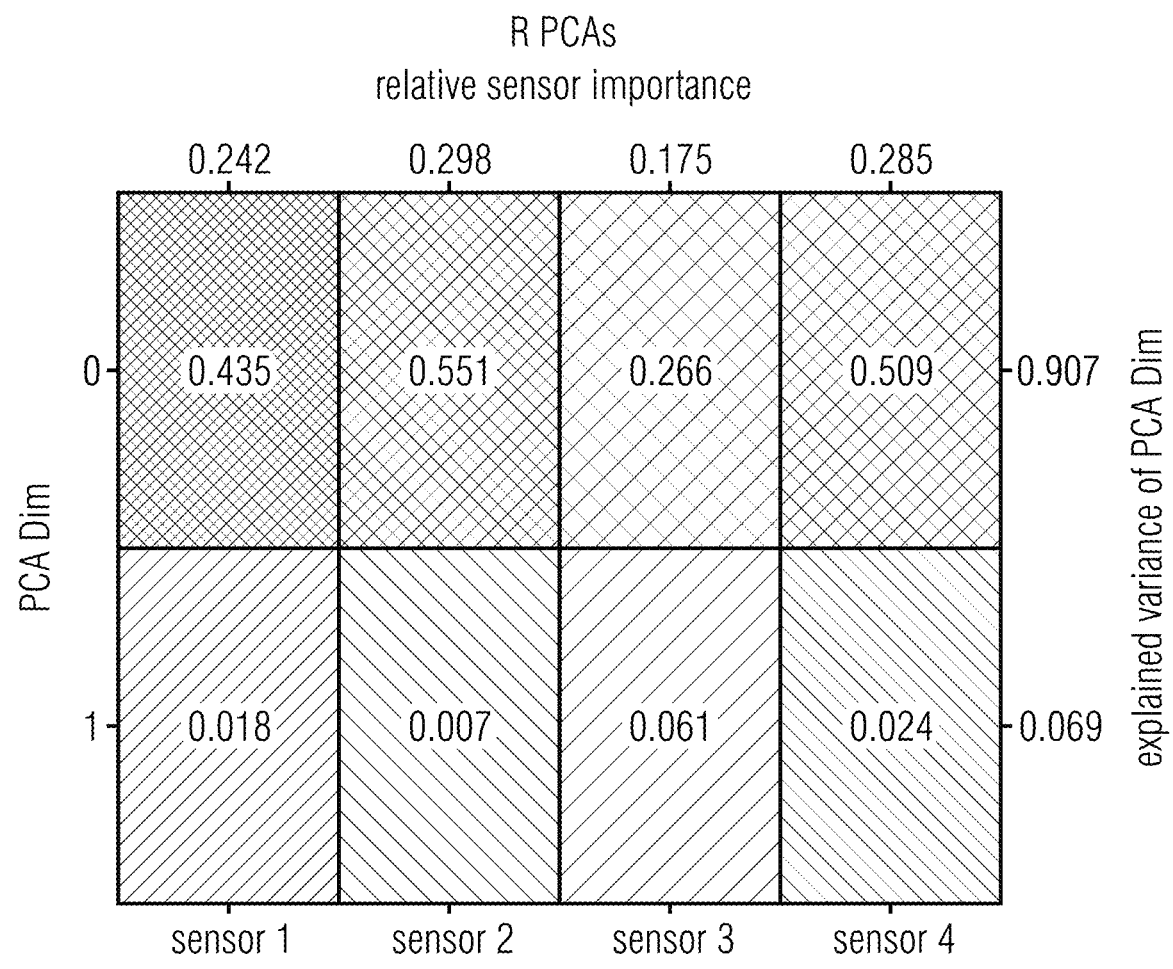
FIG. 14 illustrates the amount of information captured in a reduced feature space.

FIG. 14 illustrates the amount of information captured in a reduced feature space. The score plot in Table 1 shows that no significant amount of meaningful information is lost if the 4 dimensional features is projected on a 2-dimensional space. In the example of FIG. 14 "Dimension 0" of the PCA comprises 90.7% of the original information and "Dimension 1" of the PCA comprises 6.9% of the original information which is a total of 97.6%.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A gas sensing device for sensing one or more gases in a mixture of gases; the gas sensing device comprising:
one or more chemo-resistive gas sensors, wherein each of the gas sensors is configured for generating signal samples corresponding to a concentration of one of the one or more gases in the mixture of gases, wherein the one or more gas sensors are alternately operated in recovery phases and in sense phases, wherein at least some of the signal samples of each of the gas sensors are generated during the sense phases;
one or more heating elements for heating the gas sensors according to one or more first temperature profiles during the recovery phases and according to one or more second temperature profiles during the sense phases, wherein for each of the gas sensors a maximum temperature of the respective first temperature profile is higher than a maximum temperature of the respective second temperature profile;
an information extraction block configured for receiving the signal samples and for generating representations for the received signal samples for each of the gas sensors based on a plurality of features of the received signal samples of the respective gas sensor, wherein each of the features refers to a variation of dynamic characteristics of the received signal samples of the respective gas sensor over time, wherein each of the representations comprises a plurality of feature samples, wherein each of the feature samples is based on one or more of the features of the respective gas sensor; and
a decision making block configured for receiving the representations, wherein the decision making block comprises a weighting block and a trained model based algorithm stage, wherein the weighting block is configured for receiving the feature samples of one of the representations and for applying one or more time-variant weighting functions to each of the feature samples of the respective representation in order to calculate for each of the representations a weighted representation comprising weighted feature samples, wherein the algorithm stage comprises an input layer and an output layer, wherein the decision making block comprises one or more trained models for the algorithm stage, wherein the weighted representations for each of the gas sensors are input to the input layer of the algorithm stage, wherein the decision making block creates for each of the gas sensors sensing results based on output values of the output layer of the algorithm stage, wherein the output values for each of the gas sensors are created by using at least one of the one or more trained models at the algorithm stage so that the output values for each of the gas sensors depend on the weighted representations of each of the gas sensors.

2. The gas sensing device according to claim 1, wherein the information extraction block comprises a plurality of feature extraction stages, wherein each of the feature extraction stages is configured for calculating for one of the signal samples an output sample based on one of the features of the respective signal sample for each of the gas sensors, wherein the plurality of feature samples of one of the representations is based on the output samples of the plurality of feature extraction stages.

3. The gas sensing device according to claim 2, wherein the feature extraction stages comprise a derivative calculation stage configured for calculating a derivative of the one of the signal samples for each of the gas sensors in order to produce one of the output samples for the respective signal sample.

4. The gas sensing device according to claim 2, wherein the feature extraction stages comprise a phase space integral calculation stage configured for calculating a phase space integral of the one of the signal samples for each of the gas sensors in order to produce one of the output samples for the respective signal sample.

5. The gas sensing device according to one of the claim 2, wherein the feature extraction stages comprise a correlation calculation stage configured for calculating of
a time correlation for each of the gas sensors between the one of the signal samples and a previous signal sample of the signal samples of the respective gas sensor in order to produce one of the output samples for the respective signal sample, and/or
a spatial correlation between the one of the signal samples and one of the signal samples of another of the gas sensors in order to produce one of the output samples for the respective signal sample.

6. The gas sensing device according to one of the claim 2, wherein the feature extraction stages comprise a dynamic moment calculation stage configured for calculating of a dynamic moment of the one of the signal samples for each of the gas sensors in order to produce one of the output samples for the respective signal sample.

7. The gas sensing device according to one of the claim 2, wherein the information extraction block is configured in such way that the feature samples of one of the representations comprise all of the output samples for the corresponding signal sample.

8. The gas sensing device according to one of the claim 2, wherein the information extraction block comprises a dimensionality reduction stage, wherein each of a plurality of the output samples of one of the signal samples is fed to the dimensionality reduction stage, wherein the dimensionality reduction stage is configured to output one or more reduced output samples based on the plurality of the output samples fed to the dimensionality reduction stage, wherein a number of the reduced output samples is smaller than a number of the output samples fed to the dimensionality reduction stage, wherein a redundancy of the reduced output samples is lower than a redundancy of the output samples fed to the dimensionality reduction stage, wherein the information extraction block is configured in such way that the feature samples of one of the representations comprise all of the reduced output samples for the corresponding signal sample.

9. The gas sensing device according to claim 1, wherein the weighting block is configured for applying one of the one or more time-variant weighting functions to all of the feature samples of the respective representation in order to calculate for each of the representations a weighted representation comprising weighted feature samples.

10. The gas sensing device according to one of the claim 1, wherein the weighting block is configured for applying to at least some of the feature samples of the respective representation different time-variant weighting functions of the one or more time-variant weighting functions in order to calculate for each of the representations a weighted representation comprising weighted feature samples.

11. The gas sensing device according to claim 1, wherein the time-variant weighting functions comprise one or more window functions.

12. The gas sensing device according to claim 1, wherein the algorithm stage comprises a random decision forest using the one or more trained models.

13. The gas sensing device according to claim 1, wherein the algorithm stage comprises a neural network using the one or more trained models.

14. The gas sensing device according to claim 13, wherein the weighting block comprises a weighting function calculation block and a multiplication block,
wherein the weighting function calculation block is configured for receiving the feature samples of one of the representations,
wherein the weighting function calculation block is configured for calculating one or more of the time-variant weighting functions by calculating a function value for each of the one of the time-variant weighting functions for each time step of a plurality of time steps based on a corresponding set of feature values, wherein the corresponding set of feature values comprise a feature value corresponding to the respective time step from each of the feature samples, and
wherein the multiplication block is configured for applying to each of the feature samples of the respective representation one of the time-variant weighting functions by multiplying for each of the time steps each of the feature values corresponding to the respective time step with the function value for the respective time step in order to calculate for the one representation the weighted representation comprising weighted feature samples.

15. The gas sensing device according to claim 14, wherein the neural network is a recurrent neural network, wherein the weighting function calculation block is configured for calculating the one or more of the time-variant weighting functions by calculating the function value for each of the time-variant weighting functions for each time step of the plurality of time steps based on a hidden state of the recurrent neural network.

16. The gas sensing device according to claim 14, wherein the weighting function calculation block comprises a feed forward neural network and a softmax block,
wherein the feed forward neural network is configured for receiving the sets of feature samples and for outputting intermediate function values based on the feature samples, and
wherein the softmax block is configured for calculating the function values for the one or more time-variant weighting functions based on the intermediate function values by using a softmax function.

17. The gas sensing device according to claim 16, wherein the weighting function calculation block is configured for calculating one or more second time-variant weighting functions by calculating a second function value for one of the second time-variant weighting functions for each time step of the plurality of time steps based on a corresponding second set of feature values, wherein the corresponding second set of feature values comprise a feature value corresponding to a time step preceding the respective time step from each of the feature samples, and
wherein the multiplication block is configured for applying to each of the feature samples of the respective representation one of the second time-variant weighting functions by multiplying for each of the time steps each of the feature values corresponding to the time step preceding the respective time step with the second function value for the respective time step in order to calculate for the one representation second weighted feature samples, wherein the second weighted feature samples are added to the respective weighted representation.

18. The gas sensing device according to claim 14, wherein the neural network is a recurrent neural network, wherein the weighting function calculation block is configured for calculating the one or more second time-variant weighting functions by calculating the second function value for each of the second time-variant weighting functions for each time step of the plurality of time steps based on a hidden state of the recurrent neural network.

19. The gas sensing device according to claim 17, wherein the weighting function calculation block comprises at least one second feed forward neural network,
wherein each of the second feed forward neural network is configured for receiving one of the second sets of feature values and for outputting second intermediate function values based on one of the second sets of feature values, and
wherein the softmax block is configured for calculating the function values for the one of the time-variant weighting functions and the second function values for the one of the second time-variant weighting functions based on the intermediate function values and the second intermediate function values.

20. The gas sensing device according to claim 1, wherein at least some of the gas sensors are heated according to different first temperature profiles of the one or more first temperature profiles during the recovery phases and/or according to different second temperature profiles of the one or more second temperature profiles during the sense phases.

21. A method for operating a gas sensing device for sensing one or more gases in a mixture of gases, the gas sensing device comprising one or more chemo-resistive gas sensors, wherein the method comprises:
using each of the gas sensors for generating signal samples corresponding to a concentration of one of the one or more gases in the mixture of gases, wherein the one or more gas sensors are alternately operated in recovery phases and in sense phases, wherein at least some of the signal samples of each of the sensors are generated during the sense phases;
heating the gas sensors by using one or more heating elements according to one or more first temperature profiles during the recovery phases and according to one or more second temperature profiles during the sense phases, wherein for each of the gas sensors a maximum temperature of the respective first temperature profile is higher than a maximum temperature of the respective second temperature profile;
using an information extraction block for receiving the signal samples and for generating representations for the received signal samples for each of the gas sensors based on a plurality of features of the received signal samples of the respective gas sensor, wherein each of the features refers to a variation of dynamic characteristics of the received signal samples of the respective gas sensor over time, wherein each of the representations comprises a plurality of feature samples, wherein each of the feature samples is based on one or more of the features of the respective gas sensor;
using a decision making block, which comprises a weighting block and a trained model based algorithm stage and one or more trained models for the algorithm stage, wherein the algorithm stage has an input layer and an output layer, for creating for each of the gas sensors sensing results based on output values of the output layer of the algorithm stage; and using the weighting block for receiving the feature samples of one of the representations and for applying one or more time-variant weighting functions to each of the feature samples of the respective representation in order to calculate for each of the representations a weighted representation comprising weighted feature samples;

wherein the weighted representations for each of the gas sensors are input to the input layer of the algorithm stage, wherein the output values for the one or more gas sensors are created by using at least one of the one or more trained models at the algorithm stage so that the output values for each gas sensor of the one or more gas sensors depend on the weighted representations of each of the gas sensors.

\* \* \* \* \*